United States Patent
Cheal et al.

(10) Patent No.: US 11,565,005 B2
(45) Date of Patent: Jan. 31, 2023

(54) DOTA-HAPTEN COMPOSITIONS FOR ANTI-DOTA/ANTI-TUMOR ANTIGEN BISPECIFIC ANTIBODY PRETARGETED RADIOIMMUNOTHERAPY

(71) Applicant: MEMORIAL SLOAN KETTERING CANCER CENTER, New York, NY (US)

(72) Inventors: Sarah M. Cheal, New York, NY (US); Michael McDevitt, New York, NY (US); Ouathek Ouerfelli, New York, NY (US); Steven M. Larson, New York, NY (US); Guangbin Yang, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 362 days.

(21) Appl. No.: 16/628,068

(22) PCT Filed: Jul. 5, 2018

(86) PCT No.: PCT/US2018/040911
§ 371 (c)(1),
(2) Date: Jan. 2, 2020

(87) PCT Pub. No.: WO2019/010299
PCT Pub. Date: Jan. 10, 2019

(65) Prior Publication Data
US 2021/0145988 A1     May 20, 2021

Related U.S. Application Data

(60) Provisional application No. 62/529,363, filed on Jul. 6, 2017.

(51) Int. Cl.
| | | |
|---|---|---|
| *A61K 51/04* | (2006.01) | |
| *A61K 51/10* | (2006.01) | |
| *C07F 5/00* | (2006.01) | |
| *C07K 16/32* | (2006.01) | |
| *C07K 16/44* | (2006.01) | |

(52) U.S. Cl.
CPC ...... *A61K 51/0482* (2013.01); *A61K 51/1045* (2013.01); *C07F 5/003* (2013.01); *C07K 16/32* (2013.01); *C07K 16/44* (2013.01); *C07K 2317/31* (2013.01)

(58) Field of Classification Search
CPC ............ A61K 2123/00; A61K 2121/00; A61K 51/00; A61K 51/04; A61K 51/0482; A61K 51/1045; A61K 47/00; A61K 47/6897; A61K 47/6879; C07F 5/003; C07K 16/32; C07K 16/44; C07K 2317/31; A61P 35/00; C07D 257/02
USPC ...... 424/1.11, 1.49, 1.65, 1.69, 9.1, 9.2, 9.3, 424/9.36, 1.53; 534/7, 10–16
See application file for complete search history.

(56) References Cited

U.S. PATENT DOCUMENTS

| | | | | |
|---|---|---|---|---|
| 5,446,145 A | * | 8/1995 | Love | A61K 49/0002 540/465 |
| 5,972,307 A | * | 10/1999 | Carvalho | C07D 241/06 534/10 |
| 2010/0254987 A1 | | 10/2010 | Davis et al. | |
| 2017/0081298 A1 | * | 3/2017 | Ray | A61K 51/06 |

FOREIGN PATENT DOCUMENTS

| | | |
|---|---|---|
| WO | WO-2010/099536 A2 | 9/2010 |
| WO | WO-2012/085789 A1 | 6/2012 |
| WO | WO-2019/177970 A1 | 9/2019 |

OTHER PUBLICATIONS

Kelly Davis Orcutt et al: "Biodistribution and Clearance of Small Molecule Hapten Chelates for Pretargeted Radioimmunotherapy", Molecular Imaging and Biology, Springer-Verlag, NE, vol. 13, No. 2, Jun. 9, 2010, pp. 215-221.
Lappchen Tilman et al:"DOTA-tetrazine probes with modified linkers for tumor pretargeting", Nucl. Med. Biol., vol. 55, Dec. 1, 2017, pp. 19-26.
International Search Report and Written Opinion, PCT/US2018/040911, Memorial Sloan Kettering Cancer Center (dated Sep. 7, 2018).

\* cited by examiner

*Primary Examiner* — D. L. Jones
(74) *Attorney, Agent, or Firm* — Foley & Lardner LLP

(57) ABSTRACT

The present disclosure provides compositions and methods for the detection and treatment of cancer. Specifically, the compositions of the present technology include novel DOTA-haptens that may be complexed with a radioisotope (e.g., $^{225}$Ac). Also disclosed herein are methods of the using the DOTA-haptens of the present technology in diagnostic imaging as well as pretargeted radioimmunotherapy.

23 Claims, 12 Drawing Sheets

Figure 8

| Organ | $^{177}$Lu-DOTA-Bn ($n = 5$) | $^{225}$Ac-DOTA-Bn ($n = 5$) | p-value |
|---|---|---|---|
| Blood | 0.49 ± 0.09 | 0.33 ± 0.03 | 0.0632 |
| Tumor | 10.29 ± 2.87 | 0.82 ± 0.08 | 0.0054 |
| Heart | 0.25 ± 0.03 | 0.25 ± 0.03 | 0.3983 |
| Lungs | 0.63 ± 0.08 | 0.23 ± 0.03 | 0.0009 |
| Liver | 0.66 ± 0.10 | 2.01 ± 0.44 | 0.0085 |
| Spleen | 2.03 ± 0.56 | 0.55 ± 0.09 | 0.0152 |
| Stomach | 0.14 ± 0.03 | 0.13 ± 0.02 | 0.4426 |
| Small Intestine | 0.20 ± 0.06 | 0.10 ± 0.02 | 0.0871 |
| Large Intestine | 0.24 ± 0.09 | 0.90 ± 0.28 | 0.0257 |
| Kidneys | 0.84 ± 0.06 | 1.16 ± 0.09 | 0.0107 |
| Muscle | 0.20 ± 0.06 | 0.05 ± 0.01 | 0.0158 |
| Bone | 0.18 ± 0.05 | 0.60 ± 0.07 | 0.0005 |
| *Tumor-to-tissue ratios* | | | |
| Blood | 21.0 ± 7.0 | 2.5 ± 0.3 | |
| Heart | 41.4 ± 12.7 | 3.4 ± 0.5 | |
| Lungs | 16.2 ± 5.0 | 3.5 ± 0.6 | |
| Liver | 15.7 ± 5.0 | 0.4 ± 0.1 | |
| Spleen | 5.1 ± 2.0 | 1.5 ± 0.3 | |
| Stomach | 74.6 ± 25.6 | 6.1 ± 1.0 | |
| Small Intestine | 51.0 ± 21.3 | 9.0 ± 2.0 | |
| Large Intestine | 43.3 ± 20.1 | 0.9 ± 0.3 | |
| Kidneys | 12.3 ± 3.6 | 0.7 ± 0.1 | |
| Muscle | 50.4 ± 20.2 | 16.0 ± 2.3 | |
| Bone | 58.6 ± 22.5 | 1.4 ± 0.2 | |

(1) ▢ 1 h p.i. [$^{225}$Ac]Pr-DOTA
(2) ▨ 4 h p.i. [$^{111}$In]Pr-DOTA

Figure 12

| Organ | [$^{111}$In]1 alone<br>($n$ = 5)<br>3.38 nmol/740 kBq [20 μCi]<br>240 min p.i. |
|---|---|
| Blood | 0.03 ± 0.00 |
| Heart | 0.03 ± 0.02 |
| Lungs | 0.07 ± 0.05 |
| Liver | 0.09 ± 0.02 |
| Spleen | 0.05 ± 0.01 |
| Stomach | 0.06 ± 0.03 |
| Small Intestine | 0.19 ± 0.14 |
| Large Intestine | 0.37 ± 0.21 |
| Kidneys | 1.07 ± 0.25 |
| Muscle | 0.04 ± 0.04 |
| Bone | 0.02 ± 0.04 |

DOTA-HAPTEN COMPOSITIONS FOR ANTI-DOTA/ANTI-TUMOR ANTIGEN BISPECIFIC ANTIBODY PRETARGETED RADIOIMMUNOTHERAPY

CROSS-REFERENCE TO RELATED APPLICATIONS

This application is a National Stage Application of PCT/US2018/040811, filed Jul. 5, 2018, which claims the benefit of and priority to U.S. Provisional Patent Application No. 62/529,363, filed Jul. 6, 2017, the entire contents of which are incorporated herein by reference.

STATEMENT OF GOVERNMENT SUPPORT

This invention was made with government support under CA008748, and CA086438, awarded by the National Institutes of Health. The government has certain rights in the invention.

TECHNICAL FIELD

The present technology relates generally to compositions including novel DOTA-haptens and methods of using the same in diagnostic imaging as well as pretargeted radioimmunotherapy.

BACKGROUND

The following description of the background of the present technology is provided simply as an aid in understanding the present technology and is not admitted to describe or constitute prior art to the present technology.

Radiolabeled agents have been used as delivery vehicles of ionizing radiation to specific disease sites for over 50 years (Larson S M. *Cancer* 67:1253-1260 (1991); Britton K E. *Nucl Med Commun.* 18:992-1007 (1997)). A large number of molecules have been considered for targeted delivery of radioisotopes, including radiolabeled antibodies, antibody fragments, alterative scaffolds, and small molecules (Tolmachev V, et al. *Cancer Res.* 67:2773-2782 (2007); Birchler M T, et al., *Otolaryngol Head Neck Surg.* 136:543-548 (2007); Reubi J C, Maecke H R. *J Nucl Med.* 49:1735-1738 (2008)). Using antibodies to target poisons to tumors, e.g., radioimmunotherapy (RIT) with directly conjugated antibodies, has been challenging due in part to suboptimal tumor dose and therapeutic index (TI). Further, because of normal tissue bystander toxicity, dose escalation is not feasible and therefore such therapy results in limited anti-tumor effect. Moreover, antibodies exhibit long half-lives in the blood resulting in low tumor-to-background ratios. Antibody fragments and other smaller binding scaffolds exhibit faster blood clearance, but result in high kidney and/or liver uptake. Radiolabeled small molecule ligands generally exhibit more rapid blood clearance and lower background compared to antibodies and antibody fragments, but usually result in poor specificity due to relatively low affinities for the desired target.

In pretargeted radioimmunotherapy (PRIT), a nonradioactive bifunctional antibody with specificity for both a tumor antigen and a small molecule hapten is administered and allowed to localize to the tumor(s). After sufficient blood clearance of the antibody, a radiolabeled small molecule is administered and is captured by the pretargeted antibody. However, many small peptide and metal chelate haptens used in PRIT systems exhibit significant whole-body retention, which results in unwanted background activity that limits signal-to-background ratios for imaging and contributes to nonspecific radiation that limits the maximum tolerated dose for therapy applications (Orcutt et al., *Mol Imaging Biol* 3:215-221 (2011)).

Thus, there is a need for novel molecules that permit (a) efficient pretargeted radioimmunotherapy of solid tumors in vivo and (b) rapid clearance of radiolabeled small molecules from non-tumor tissue.

SUMMARY OF THE PRESENT TECHNOLOGY

In one aspect, the present disclosure provides a compound of Formula I

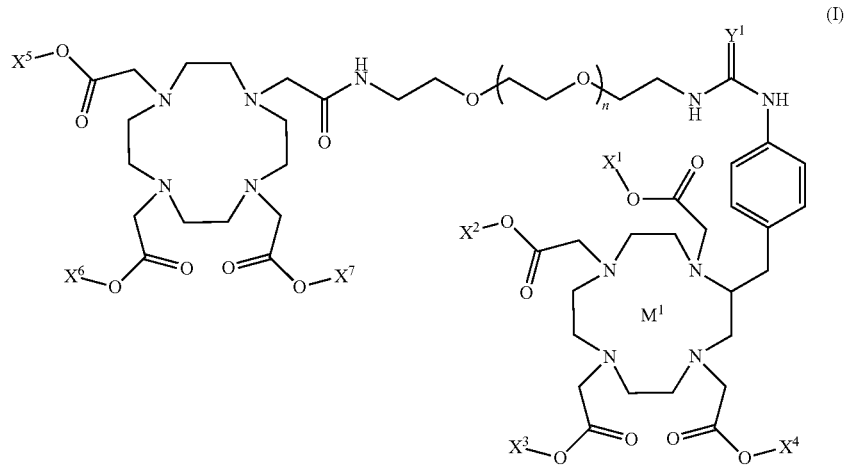

or a pharmaceutically acceptable salt thereof, wherein $M^1$ is $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $160Gd^{3+}$, or $^{160}Gd^3$; $X^1$, $X^2$, $X^3$, and $X^4$ are each independently a lone pair of electrons (i.e. providing an oxygen anion) or H; $X^5$, $X^6$, and $X^7$ are each independently a lone pair of electrons (i.e. providing an oxygen anion) or H; $Y^1$ is O or S; and n is 1, 2, 3, 4, 5, 6, 7, 8, 9, 10, 11, 12, 13, 14, 15, 16, 17, 18, 19, 20, 21, or 22. In certain embodiments, n is 3. In certain embodiments, n is 3. In certain embodiments, n is 3 and $Y^1$ is S.

In some embodiments of the compound, at least two of $X^1$, $X^2$, $X^3$, and $X^4$ are each independently a lone pair of electrons. In certain embodiments of the compound, three of $X^1$, $X^2$, $X^3$, and $X^4$ are each independently a lone pair of electrons and the remaining $X^1$, $X^2$, $X^3$, or $X^4$ is H.

In another aspect, the present disclosure provides a bischelate comprising any of the above compounds of Formula I and a radionuclide cation. In some embodiments, the bischelate is of Formula II antigen target. In any of the above embodiments of the complexes disclosed herein, the bispecific antibody may be an infinite binder. In some embodiments, the bispecific antibody comprises an antigen binding fragment of C825 (See Cheal et al., *Mol Cancer Ther.* 13(7):1803-12 (2014)) or 2D12.5 (Corneillie et al., *J. Inorganic Biochemistry* 100:882-890 (2006)). Additionally or alternatively, in any of the above embodiments of the complexes disclosed herein, the bispecific antibody comprises an antigen binding fragment of C825 with a G54C substitution. Additionally or alternatively, in any of the above embodiments of the

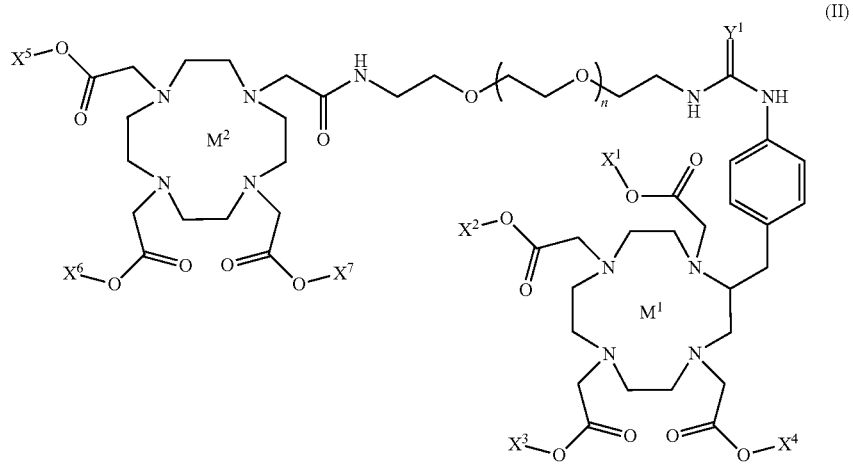

(II)

or a pharmaceutically acceptable salt thereof, wherein $M^1$ is $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $160Gd^{3+}$; $M^2$ is the radionuclide cation; $X^1$, $X^2$, $X^3$, and $X^4$ are each independently a lone pair of electrons (i.e. providing an oxygen anion) or H; $X^5$, $X^6$, and $X^7$ are each independently a lone pair of electrons (i.e. providing an oxygen anion) or H; $Y^1$ is O or S; and n is 1, 2, 3, 4, 5, 6, 7, 8, 9, 10, 11, 12, 13, 14, 15, 16, 17, 18, 19, 20, 21, or 22. In certain embodiments, n is 3. In certain embodiments, n is 3 and $Y^1$ is S.

In some embodiments of the bischelate, at least two of $X^5$, $X^6$, and $X^7$ are each independently a lone pair of electrons. Additionally or alternatively, in some embodiments of the bischelate, the radionuclide cation is a divalent cation or a trivalent cation. The radionuclide cation may be an alpha particle-emitting isotope, a beta particle-emitting isotope, an Auger-emitter, or a combination of any two or more thereof. Examples of alpha particle-emitting isotopes include, but are not limited to, $^{213}Bi$, $^{211}At$, $^{225}Ac$, $^{152}Dy$, $^{212}Bi$, $^{223}Ra$, $^{219}Rn$, $^{215}Po$, $^{211}Bi$, $^{221}Fr$, $^{217}At$, and $^{255}Fm$. Examples of beta particle-emitting isotopes include, but are not limited to, $^{86}Y$, $^{90}Y$, $^{89}Sr$, $^{165}Dy$, $^{186}Re$, $^{88}Re$, $^{177}Lu$, and $^{67}Cu$. Examples of Auger-emitters include $^{111}In$, $^{67}Ga$, $^{51}Cr$, $^{58}Co$, $^{99m}Tc$, $^{103m}Rh$, $^{195m}Pt$, $^{119}Sb$, $^{161}Ho$, $^{189m}Os$, $^{192}Ir$, $^{201}Tl$, and $^{203}Pb$. In some embodiments of the bischelate, the radionuclide cation is $^{68}G$, $^{227}Th$, or $^{64}CU$.

In another aspect, the present disclosure provides a complex comprising the compound of Formula I and a bispecific antibody that recognizes and binds to the compound and a tumor antigen target. The present disclosure also provides a complex comprising the bischelate of Formula II and a bispecific antibody that binds to the bischelate and a tumor complexes disclosed herein, the bispecific antibody comprises an antigen binding fragment of 2D12.5 with a G54C substitution.

In any of the above embodiments of the complexes disclosed herein, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM. Additionally or alternatively, in some embodiments of the complex, the bispecific antibody binds to the compound or the bischelate with a $K_d$ that is lower than or equal to 100 nM-95 nM, 95-90 nM, 90-85 nM, 85-80 nM, 80-75 nM, 75-70 nM, 70-65 nM, 65-60 nM, 60-55 nM, 55-50 nM, 50-45 nM, 45-40 nM, 40-35 nM, 35-30 nM, 30-25 nM, 25-20 nM, 20-15 nM, 15-10 nM, 10-5 nM, 5-1 nM, 1 nM-950 pM, 950 pM-900 pM, 900 pM-850 pM, 850 pM-800 pM, 800 pM-750 pM, 750 pM-700 pM, 700 pM-650 pM, 650 pM-600 pM, 600 pM-550 pM, 550 pM-500 pM, 500 pM-450 pM, 450 pM-400 pM, 400 pM-350 pM, 350 pM-300 pM, 300 pM-250 pM, 250 pM-200 pM, 200 pM-150 pM, 150 pM-100 pM, 100 pM-50 pM, 50 pM-40 pM, 40 pM-30 pM, 30 pM-20 pM, 20 pM-10 pM, 9 pM, 8 pM, 7 pM, 6 pM, 5 pM, 4 pM, 3 pM, 2.5 pM, 2 pM, 1.5 pM, or 1 pM.

In one aspect, the present disclosure provides a method for detecting solid tumors in a subject in need thereof comprising (a) administering to the subject an effective amount of a complex comprising the bischelate of Formula II and a bispecific antibody that binds to the bischelate and a tumor antigen target, wherein the complex is configured to localize to a solid tumor expressing the tumor antigen target recognized by the bispecific antibody of the complex; and (b) detecting the presence of solid tumors in the subject by detecting radioactive levels emitted by the complex that are higher than a reference value. In some embodiments, the subject is human.

In another aspect, the present disclosure provides a method for selecting a subject for pretargeted radioimmunotherapy comprising (a) administering to the subject an effective amount of a complex comprising the bischelate of Formula II and a bispecific antibody that binds to the bischelate and a tumor antigen target, wherein the complex is configured to localize to a solid tumor expressing the tumor antigen target recognized by the bispecific antibody of the complex; (b) detecting radioactive levels emitted by the complex; and (c) selecting the subject for pretargeted radioimmunotherapy when the radioactive levels emitted by the complex are higher than a reference value. In some embodiments, the subject is human.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having cancer. The cancer may be selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, and head-and-neck cancer. In some embodiments, the brain cancer is a pituitary adenoma, a meningioma, a neuroblastoma, or a craniopharyngioma.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally or intranasally. In certain embodiments, the complex is administered into the cerebral spinal fluid or blood of the subject.

In some embodiments of the methods disclosed herein, the radioactive levels emitted by the complex are detected between 4 to 24 hours after the complex is administered. In certain embodiments of the methods disclosed herein, the radioactive levels emitted by the complex are expressed as the percentage injected dose per gram tissue (% ID/g). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with cancer comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of Formula II to the subject, wherein the bischelate is configured to bind to the anti-DOTA bispecific antibody. In some embodiments, the method further comprises administering an effective amount of a clearing agent to the subject prior to administration of the bischelate. The clearing agent may be a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.). In some embodiments, the subject is human.

Additionally or alternatively, in some embodiments of the method, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM.

Additionally or alternatively, in some embodiments of the method, the anti-DOTA bispecific antibody and/or the bischelate is administered intravenously, intramuscularly, intraarterially, intrathecally, intracapsularly, intraorbitally, intradermally, intraperitoneally, transtracheally, subcutaneously, intracerebroventricularly, orally or intranasally.

In one aspect, the present disclosure provides a method for increasing tumor sensitivity to radiation therapy in a subject diagnosed with cancer comprising administering to the subject an effective amount of a complex comprising the bischelate of Formula II and a bispecific antibody that recognizes and binds to the bischelate and a tumor antigen target, wherein the complex is configured to localize to a tumor expressing the tumor antigen target recognized by the bispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments, the subject is human.

In another aspect, the present disclosure provides a method for treating cancer in a subject in need thereof comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of Formula II to the subject, wherein the bischelate is configured to bind to the anti-DOTA bispecific antibody. In certain embodiments, the method further comprises administering an effective amount of a clearing agent to the subject prior to administration of the bischelate. Also provided herein are methods for treating cancer in a subject in need thereof comprising administering to the subject an effective amount of a complex comprising the bischelate of Formula II and a bispecific antibody that recognizes and binds to the bischelate and a tumor antigen target, wherein the complex is configured to localize to a tumor expressing the tumor antigen target recognized by the bispecific antibody of the complex.

The methods for treating cancer may further comprise sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagon ists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11. In some embodiments, the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, and head-and-neck cancer. In some embodiments, the subject is human.

Also disclosed herein are kits containing components suitable for treating or diagnosing cancer in a patient. In one aspect, the kits comprise a DOTA hapten composition of the present technology, at least one anti-DOTA bispecific antibody, and instructions for use. The kits may further comprise a clearing agent (e.g., 500 kDa aminodextran conjugated to DOTA) and/or one or more radionuclides.

BRIEF DESCRIPTION OF THE DRAWINGS

FIG. 8 shows a comparison of $^{225}$Ac-DOTA-Bn and $^{177}$Lu-DOTA-Bn pretargeting with anti-GD2-DOTA-PRIT. Female athymic nude mice bearing subcutaneous GD2-expressing IMR-32 human neuroblastoma xenografts in the right-hand flank were injected intravenously (i.v.) via the lateral tail-vein with three separate reagents: (1) hu3F8-C825 (0.25 mg, 1.19 nmol) [t=−28 hours (h)], followed by (2) 0.1 mg 500 kD-dextran-DOTA-Bn(Y) (0.2 nmol of CA; 146 DOTA-Bn(Y)/mol of dextran, 29 nmol of DOTA-Bn (Y)) [t=−4 h] and (3) an equimolar amount of either $^{177}$Lu- or $^{225}$Ac-DOTA-Bn (50 µCi and 100 µCi of $^{177}$Lu and $^{225}$Ac, respectively, 8-10 pmol) at [t=0 h]. Mice were sacrificed at 24 h post-injection of radiotracer for biodistribution assay of tumor and select normal tissues. The average tumor masses were as follows (presented as average ±SD): 0.77±0.62 g and 0.49±0.28 g for $^{177}$Lu and $^{225}$Ac cohorts, respectively. Activity concentration data are expressed as the mean % ID/g standard error of the mean (SEM). Errors for the tumor-to-tissue ratios are calculated as the geometric mean of the standard errors of the mean. Student's t-test p-values highlighted in bold are considered significant (p<0.05).

Asterisk (*) indicates mouse required euthanasia or was discovered deceased. Data is presented as mean ±SD.

Figure 11:
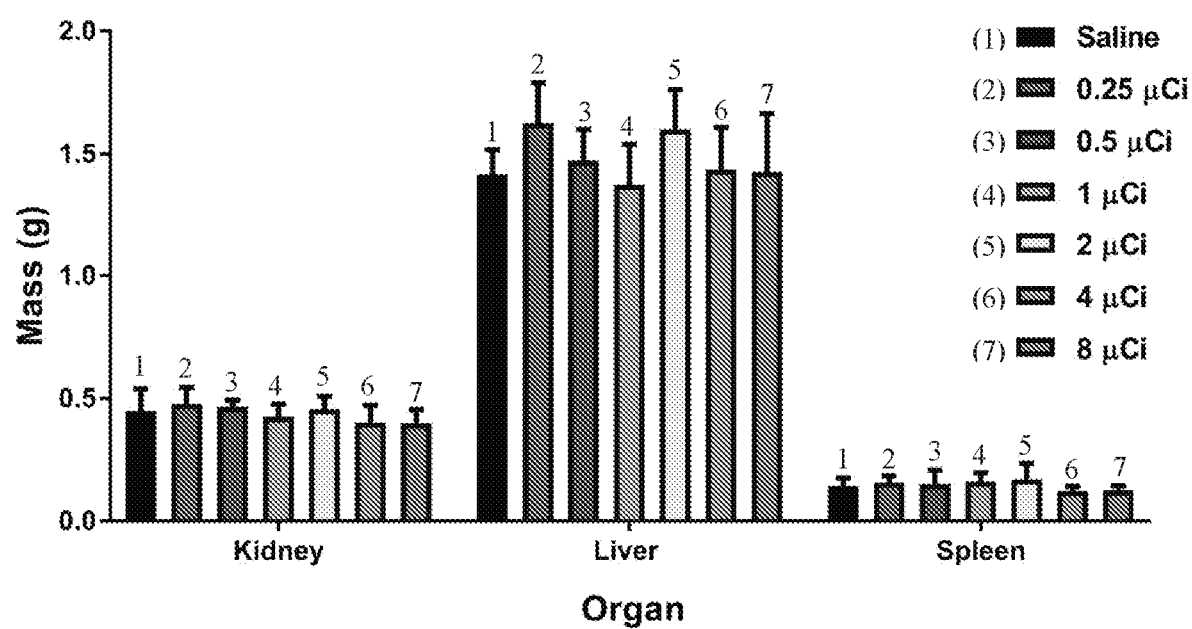

FIG. 11 shows select organ weights at 145 days taken at necropsy of tumor-free healthy female athymic nude mice treated with varying dose levels of [$^{225}$Ac]*Proteus*-DOTA. No significant group differences were observed in organ weights.

FIG. 12 shows the biodistribution of [$^{111}$In]*Proteus*-DOTA (740 kBq [20 µCi]/3.38 nmol) at 240 min p.i. (n=5 mice; given i.v.) in tumor-free healthy athymic nu/nu female mice.

DETAILED DESCRIPTION

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

The compositions of the present technology include novel DOTA-haptens that are useful in diagnostic imaging/dosimetry and PRIT (e.g., alpha-particle radioimmunotherapy). The compositions disclosed herein permit efficient anti-DOTA-bispecific antibody mediated tumor pretargeting in vivo of actinium-225 ($^{225}$Ac) for targeted radiotherapy. The DOTA-PRIT platform entails a three-step pretargeting strategy including the administration of (1) an IgG-single chain variable fragment (scFv) bispecific antibody construct (IgG-scFv) comprising antibody sequences for an anti-tumor antigen antibody (the IgG-portion) and a pM-affinity anti-DOTA-hapten single chain variable fragment scFv "C825", (2) a 500 kD-dextran-DOTA-hapten clearing agent, and (3) a radiolabeled DOTA hapten composition of the present technology.

Previous studies have demonstrated that anti-GPA33-DOTA-PRIT could be used to pretarget $^{177}$Lu- or $^{86}$Y—S-2-(4-aminobenzyl)-1,4,7,10-tetraazacyclododecane tetraacetic acid chelate (DOTA-Bn) hapten for theranostic beta-particle radioimmunotherapy (RIT) or in vivo positron emission tomography (PET) of athymic nude mice bearing GPA33-expressing colon cancer xenografts, respectively. However, pretargeting with $^{225}$Ac-DOTA-Bn in vivo using a model PRIT system led to unremarkable tumor uptake of $^{225}$Ac-DOTA-Bn 24 hours post-injection (<1% ID/g). See FIG. 8. Thus, conventional DOTA-haptens are ill-suited for DOTA-PRIT radiotherapy applications involving high linear energy transfer (LET) alpha particle-emitting isotopes such as $^{225}$Ac.

In contrast, the DOTA hapten compositions disclosed herein (a) permit efficient in vivo pretargeted alpha-particle radiotherapy of solid tumors, (b) exhibit complete renal clearance with no unwanted kidney/whole-body retention, and (c) can bind to an anti-DOTA bispecific antibody (e.g., anti-HER2-C825) with high affinity (i.e., the Ac-$^{225}$-DOTA-moiety of the DOTA hapten composition of the present technology does not sterically block the interactions between the lutetium-DOTA moiety of the DOTA hapten composition and an anti-DOTA bispecific antibody).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca2+, Mg$^{2+}$, Zn$^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

As used herein, the "administration" of an agent or drug to a subject includes any route of introducing or delivering to a subject a compound to perform its intended function. Admin istration can be carried out by any suitable route, including orally, intranasally, parenterally (intravenously, intramuscularly, intraperitoneally, or subcutaneously), rectally, or topically. Admin istration includes self-administration and the administration by another.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes "intact immunoglobulins") and "antigen binding fragments" specifically bind to a molecule of interest (or a group of highly similar molecules of interest) to the substantial exclusion of binding to other molecules (for example, antibodies and antibody fragments that have a binding constant for the molecule of interest that is about $10^3$ $M^{-1}$ times greater, about $10^4$ $M^{-1}$ times greater or about $10^5$ $M^{-1}$ times greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, $3^{rd}$ Ed., W. H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds a target protein (e.g., HER2) or molecule (e.g., DOTA) will have a specific $V_H$ region and $V_L$ region sequence, and thus specific CDR sequences. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). Examples of antibodies include monoclonal antibodies, polyclonal antibodies, humanized antibodies, chimeric antibodies, recombinant antibodies, multispecific antibodies, bispecific antibodies, and antibody fragments. An antibody specifically binds to an antigen.

A "bispecific antibody" is an antibody that can bind simultaneously to two different antigens. Bispecific antibodies (BsAb) and bispecific antibody fragments (BsFab) may have at least one arm that specifically binds to, for example, a tumor-associated antigen (e.g., HER2) and at least one other arm that specifically binds to a targetable conjugate that bears a therapeutic or diagnostic agent (e.g., Proteus-DOTA). A variety of different bispecific antibody structures are known in the art. In some embodiments, each binding moiety in a bispecific antibody comprises a $V_H$ and/or $V_L$ region from different monoclonal antibodies. In some embodiments, the bispecific antibody comprises an immunoglobulin molecule having $V_H$ and/or $V_L$ regions that contain CDRs from a first monoclonal antibody, and an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404, 097; WO 93/11161; and 30 Hollinger et al., *Proc. Natl. Acad. Sci. USA*, 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ (scF$_v$)). Bird et al. (1988) *Science* 242:423-426 and Huston et al. (1988) *Proc. Natl. Acad Sci. USA* 85:5879-5883. Such single-chain antibodies can be prepared by recombinant techniques or enzymatic or chemical cleavage of intact antibodies.

As used herein, the terms "intact antibody" or "intact immunoglobulin" mean an antibody or immunoglobulin that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, an "antigen" refers to a molecule to which an antibody can selectively bind. The target antigen may be a protein (e.g., an antigenic peptide), carbohydrate, nucleic acid, lipid, hapten, or other naturally occurring or synthetic compound. An antigen may also be administered to an animal subject to generate an immune response in the subject.

As used herein, the term "antigen binding fragment" refers to a fragment of a whole immunoglobulin structure which possesses a part of a polypeptide responsible for binding to an antigen. Examples of the antigen binding fragment useful in the present technology include scFv, $(scFv)_2$, scFvFc, Fab, Fab' and $F(ab')_2$, diabodies; linear antibodies; single-chain antibody molecules; and multispecific antibodies formed from antibody fragments.

By "binding affinity" is meant the strength of the total noncovalent interactions between a single binding site of a molecule (e.g., an antibody) and its binding partner (e.g., an antigen). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, a "clearing agent" is an agent that binds to excess bifunctional antibody that is present in the blood compartment of a subject to facilitate rapid clearance via kidneys. The use of the clearing agent prior to hapten administration facilitates better tumor-to-background ratios in PRIT systems. Examples of clearing agents include 500 kD-dextran-DOTA-Bn(Y) (Orcutt et al., Mol Cancer Ther. 11(6): 1365-1372 (2012)), 500 kD aminodextran-DOTA conjugate, antibodies against the pretargeting antibody, etc.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" of a composition, is a quantity sufficient to achieve a desired prophylactic or therapeutic effect, e.g., an amount which results in the decrease in the symptoms associated with a disease that is being treated, e.g., the diseases or medical conditions associated with target polypeptide (e.g., breast cancer, colorectal cancer, brain cancer etc.). The amount of a composition of the present technology administered to the subject will depend on the degree, type and severity of the disease and on the characteristics of the individual, such as general health, age, sex, body weight and tolerance to drugs. The skilled artisan will be able to determine appropriate dosages depending on these and other factors. The compositions of the present technology can also be administered in combination with one or more additional therapeutic compounds.

As used herein, the term "epitope" means an antigenic determinant capable of specific binding to an antibody. Epitopes usually consist of chemically active surface groupings of molecules and usually have specific three dimensional structural characteristics, as well as specific charge characteristics.

As used herein, an "infinite binder" refers to an anti-metal chelate bispecific antibody that is characterized by the formation of a highly specific permanent bond between the bispecific antibody and the metal chelate upon binding. See Corneillie et al., *J. Inorganic Biochemistry* 100:882-890 (2006).

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, "specifically binds" refers to a molecule (e.g., an antibody) which recognizes and binds another molecule (e.g., an antigen), but does not substantially recognize and bind other molecules. The terms "specific binding," "specifically binds to," or is "specific for" a particular molecule (e.g., an antigen, or an epitope on an antigen), as used herein, can be exhibited, for example, by a molecule having a $K_d$ for the molecule to which it binds to of about $10^{-4}$M, $10^{-5}$M, $10^{-6}$M, $10^{-7}$M, $10^{-8}$M, $10^{-9}$M, $10^{-10}$M, $10^{-11}$M, or $10^{-12}$M.

As used herein, the terms "subject," "individual," or "patient" are used interchangeably and refer to an individual organ ism, a vertebrate, a mammal, or a human. In certain embodiments, the individual, patient or subject is a human.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. By "treating a cancer" is meant that the symptoms associated with the cancer are, e.g., alleviated, reduced, cured, or placed in a state of remission.

It is also to be appreciated that the various modes of treatment of diseases as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Pretargeted Radioimmunotherapy (PRIT)

Pre-targeting is a multistep process that resolves the slow blood clearance of tumor targeting antibodies, which contributes to undesirable toxicity to normal tissues such as bone marrow. In pre-targeting, a radionuclide or other diagnostic or therapeutic agent is attached to a small hapten. A pre-targeting bispecific antibody, which has binding sites for the hapten as well as a target antigen, is administered first. Unbound antibody is then allowed to clear from circulation and the hapten is subsequently administered.

DOTA-PRIT has been used to effectively target a beta-emitting radioisotope (e.g., lutetium-177) to GD2- or GPA33-expressing human carcinoma xenografts, thus reducing toxicity to normal tissues such as bone marrow and kidney. Beta-particle emissions (e.g., from $^{177}$Lu-DOTA-Bn haptens) are considered to be low linear energy transfer, with a range of 1-10 nm and 0.1-1 MeV energy. DOTA-PRIT is optimally suited for targeting beta-particle emitting radioactive isotopes of lutetium and yttrium ($^{177}$Lu and $^{90}$Y, respectively) because anti-DOTA C825 (an anti-DOTA scFv) binds DOTA-complexes containing such radiolanthanides with pM affinity.

However, solid tumors are generally radio-resistant. Alpha-particle radiotherapy (e.g., with $^{225}$Ac-DOTA-haptens) on the other hand results in highly potent cell-killing activity with minimal collateral damage via high linear energy transfer alpha particle emissions with a range of 50-80 microns and 5-8 MeV energy. Unlike beta-particles that can deposit their energy over a longer distance, alpha-particle radiotherapy has a high therapeutic potential against small-volume tumors, including minimal residual disease which can be a major cause of cancer relapse. Thus there is a need to increase the effectiveness of DOTA-PRIT radiotherapy with alpha-particle emitters, which have greater therapeutic potential compared to beta-particles.

An inherent limitation of C825 is the variation in binding affinity that the scFv has for various anti-DOTA-haptens, which is highly dependent on the ionic radius of the trivalent rare earth. Previous modeling studies have demonstrated that a hapten-binding affinity of 100 pM is needed for efficient delivery of ionizing radiation in PRIT (assuming conditions of high antigen density and saturating BsAb dose), specifically to achieve near-maximal hapten retention in vascular tumors and micrometastases. C825 was shown to bind DOTA-Bn [S-2-(4-aminobenzyl)-1,4,7,10-tetraazacyclododecane tetraacetic acid chelate] complexes of Y, Lu, or Gd with a $K_d$ (equilibrium dissociation constant, as mean ±SD) of 15.4±2.0 pM, 10.8±2.5 pM, or 34.0±5.3 pM, respectively. In contrast, the $K_d$ for DOTA-Bn complexes containing In or Ga was 1.01±0.04 nM or 52±12 nM. Thus, DOTA-PRIT is well suited for targeting beta-particle emitters yttrium-90 and lutetium-177, but is less likely to be compatible with an alpha-particle emitter (e.g., Actinium isotopes).

Although the $K_d$ for $^{225}$Ac was not characterized in vitro, preliminary experiments have shown that pretargeting with $^{225}$Ac-DOTA-Bn in vivo using a model DOTA-PRIT system (anti-GD2-DOTA-PRIT) led to statistically significant (p≤0.005; unpaired, two-tailed Student's t-test) and unremarkable tumor uptake of $^{225}$Ac-DOTA-Bn 24 hours post-injection compared to equimolar administered $^{177}$Lu-DOTA-Bn (as % ID/g; average±standard deviation (SD); for $^{225}$Ac-DOTA-Bn (n=5): 0.82±0.17; for $^{177}$Lu-DOTA-Bn (n=5): 10.29±2.87). See FIG. 8. There were no major differences observed in normal tissue such as blood or kidney (for blood: 0.33±0.03 or 0.49±0.09 for $^{225}$Ac- or $^{177}$Lu-DOTA-Bn, respectively; for kidney: 0.65±0.15 or 0.83±0.10 for $^{225}$Ac- or $^{177}$Lu-DOTA-Bn, respectively; both p>0.05), suggesting that the in vivo fate of the two tracers was similar, and in vivo stability was likely not a limiting factor for tumor localization.

Compositions of the Present Technology

DOTA is a macrocyclic chelating agent that forms stable metal complexes that are irreversible under physiological conditions. DOTA has a molecular weight of 405 Daltons, and exhibits rapid diffusion and renal clearance. DOTA and its variants chelate a wide range of metals including paramagnetic metals and radionuclides. Exemplary metals include yttrium, indium, gallium, gadolinium, europium, terbium, lutetium, copper, bismuth, actinium and all lanthanide metals.

In one aspect, the present disclosure provides a compound of Formula I

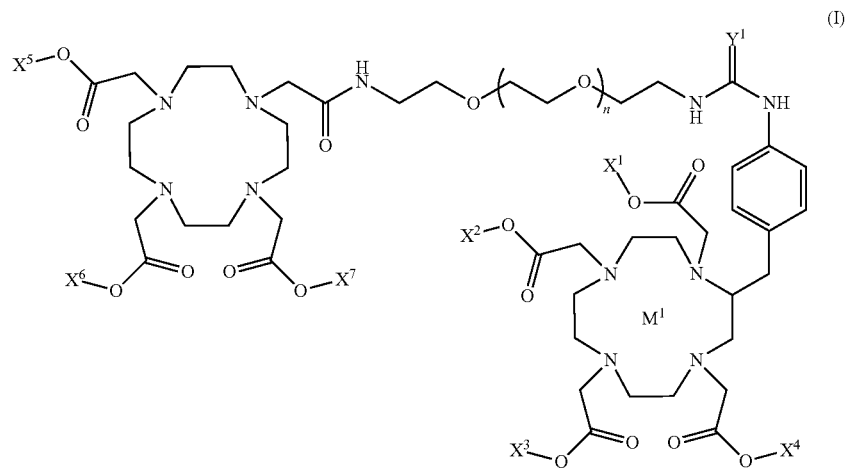

(I)

or a pharmaceutically acceptable salt thereof, wherein $M^1$ is $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $^{160}Gd^{3+}$; $X^1$, $X^2$, $X^3$, and $X^4$ are each independently a lone pair of electrons (i.e. providing an oxygen anion) or H; $X^5$, $X^6$, and $X^7$ are each independently a lone pair of electrons (i.e. providing an oxygen anion) or H; $Y^1$ is O or S; and n is 1, 2,3, 4, 5,6,7, 8, 9,10, 11, 12, 13, 14, 15, 16, 17, 18, 19, 20, 21, or 22. In certain embodiments, n is 3. In certain embodiments, n is 3 and $Y^1$ is S.

In some embodiments of the compound, at least two of $X^1$, $X^2$, $X^3$, and $X^4$ are each independently a lone pair of electrons. In certain embodiments of the compound, three of $X^1$, $X^2$, $X^3$, and $X^4$ are each independently a lone pair of electrons and the remaining $X^1$, $X^2$, $X^3$, or $X^4$ is H.

In another aspect, the present disclosure provides a bischelate comprising any of the above compounds of Formula I and a radionuclide cation. In some embodiments, the compound of Formula I can bind a radionuclide cation with a $K_d$ of about 1pM-1 nM (e.g., about 1-10 pM; 1-100 pM; 5-50 pM; 100-500 pM; or 500 pM-1 nM). In some embodiments, the $K_d$ is in the range of about 1 nM to about 1pM, for example, no more than about 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 150 pM, 100 pM, 90 pM, 80 pM, 70 pM, 60 pM, 50 pM, 40 pM, 30 pM, 20 pM, 10 pM, 9pM, 8pM, 7pM, 6pM, 5pM, 4pM, 3 pM, 2.5 pM, 2pM, or 1pM. In some embodiments, the bischelate is of Formula II bischelate, the radionuclide cation is a divalent cation or a trivalent cation. The radionuclide cation may be an alpha particle-emitting isotope, a beta particle-emitting isotope, an Auger-emitter, or a combination of any two or more thereof. Examples of alpha particle-emitting isotopes include, but are not limited to, $^{213}Bi$, $^{211}At$, $^{225}Ac$, $^{152}Dy$, $^{212}Bi$, $^{223}Ra$, $^{219}Rn$, $^{215}Po$, $^{211}Bi$, $^{221}Fr$, $^{217}At$, and $^{255}Fm$. Examples of beta particle-emitting isotopes include, but are not limited to, $^{86}Y$, $^{90}Y$, $^{89}Sr$, $^{165}Dy$, $^{186}Re$, $^{188}Re$, $^{177}Lu$, and $^{67}Cu$. Examples of Auger-emitters include $^{111}In$, $^{67}Ga$, $^{51}Cr$, $^{58}Co$, $^{99m}Tc$, $^{103m}Rh$, $^{195m}Pt$, $^{119}Sb$, $^{161}Ho$, $^{189m}Os$, $^{192}Ir$, $^{201}Tl$, and $^{203}Pb$. In some embodiments of the bischelate, the radionuclide cation is $^{68}Ga$, $^{227}Th$, or $^{64}Cu$.

In some embodiments, the radionuclide cation has a decay energy in the range of 20 to 6,000 keV. Decay energies can be within the range of 60 to 200 keV for an Auger emitter, 100-2,500 keV for a beta emitter, and 4,000-6,000 keV for an alpha emitter. Maximum decay energies of useful beta-particle-emitting nuclides can range from 20-5,000 keV, 100-4,000 keV, or 500-2,500 keV. Decay energies of useful Auger-emitters can be <1,000 keV, <100 keV, or <70 keV. Decay energies of useful alpha-particle-emitting radionuclides can range from 2,000-10,000 keV, 3,000-8,000 keV, or 4,000-7,000 keV.

In another aspect, the present disclosure provides a complex comprising the compound of Formula I and a bispecific antibody that recognizes and binds to the compound and a tumor antigen target. The present disclosure also provides a complex comprising the bischelate of Formula II and a bispecific antibody that binds to the bischelate and a tumor

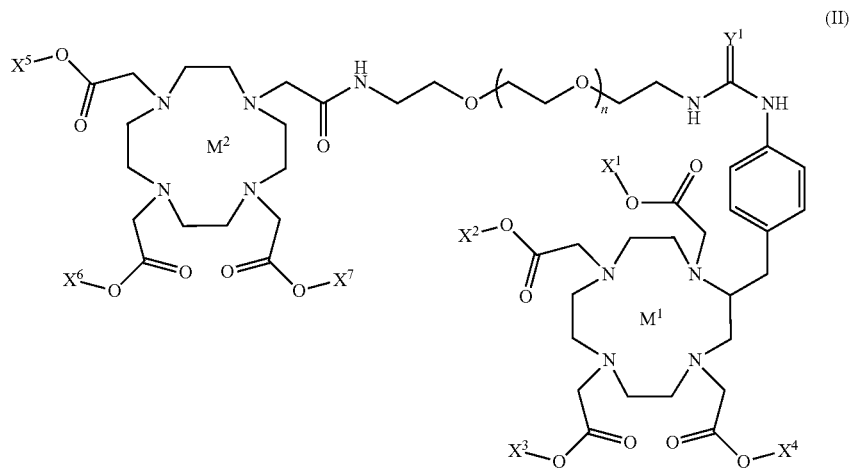

(II)

or a pharmaceutically acceptable salt thereof, wherein $M^1$ is $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^3$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $^{160}Gd^{3+}$; $M^2$ is the radionuclide cation; $X^1$, $X^2$, $X^3$, and $X^4$ are each independently a lone pair of electrons (i.e. providing an oxygen anion) or H; $X^5$, $X^6$, and $X^7$ are each independently a lone pair of electrons (i.e. providing an oxygen anion) or H; $Y^1$ is O or S; and n is 1, 2, 3, 4, 5, 6, 7, 8, 9, 10, 11, 12, 13, 14, 15, 16, 17, 18, 19, 20, 21, or 22. In certain embodiments, n is 3. In certain embodiments, n is 3 and $Y^1$ is S.

In some embodiments of the bischelate, at least two of $X^5$, $X^6$, and $X^7$ are each independently a lone pair of electrons. Additionally or alternatively, in some embodiments of the antigen target. In any of the above embodiments of the complexes disclosed herein, the bispecific antibody may be an infinite binder. In some embodiments, the bispecific antibody comprises an antigen binding fragment of C825 (See Cheal et al., *Mol Cancer Ther.* 13(7):1803-12 (2014)) or 2D12.5 (Corneillie et al., *J. Inorganic Biochemistry* 100:882-890 (2006)). Additionally or alternatively, in any of the above embodiments of the complexes disclosed herein, the bispecific antibody comprises an antigen binding fragment of C825 with a G54C substitution. Additionally or alternatively, in any of the above embodiments of the complexes disclosed herein, the bispecific antibody comprises an antigen binding fragment of 2D12.5 with a G54C substitution.

In any of the above embodiments of the complexes disclosed herein, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM. Additionally or alternatively, in some embodiments of the complex, the bispecific antibody binds to the compound or the bischelate with a $K_d$ that is lower than or equal to 100 nM-95 nM, 95-90 nM, 90-85 nM, 85-80 nM, 80-75 nM, 75-70 nM, 70-65 nM, 65-60 nM, 60-55 nM, 55-50 nM, 50-45 nM, 45-40 nM, 40-35 nM, 35-30 nM, 30-25 nM, 25-20 nM, 20-15 nM, 15-10 nM, 10-5 nM, 5-1 nM, 1 nM-950 pM, 950 pM-900 pM, 900 pM-850 pM, 850 pM-800 pM, 800 pM-750 pM, 750 pM-700 pM, 700 pM-650 pM, 650 pM-600 pM, 600 pM-550 pM, 550 pM-500 pM, 500 pM-450 pM, 450 pM-400 pM, 400 pM-350 pM, 350 pM-300 pM, 300 pM-250 pM, 250 pM-200 pM, 200 pM-150 pM, 150 pM-100 pM, 100 pM-50 pM, 50 pM-40 pM, 40 pM-30 pM, 30 pM-20 pM, 20 pM-10 pM, 9 pM, 8 pM, 7 pM, 6 pM, 5 pM, 4 pM, 3 pM, 2.5 pM, 2 pM, 1.5 pM, or 1 pM.

Diagnostic and Therapeutic Methods of the Present Technology

In one aspect, the present disclosure provides a method for detecting solid tumors in a subject in need thereof comprising (a) administering to the subject an effective amount of a complex comprising the bischelate of Formula II and a bispecific antibody that binds to the bischelate and a tumor antigen target, wherein the complex is configured to localize to a solid tumor expressing the tumor antigen target recognized by the bispecific antibody of the complex; and (b) detecting the presence of solid tumors in the subject by detecting radioactive levels emitted by the complex that are higher than a reference value. In some embodiments, the subject is human.

In another aspect, the present disclosure provides a method for selecting a subject for pretargeted radioimmunotherapy comprising (a) administering to the subject an effective amount of a complex comprising the bischelate of Formula II and a bispecific antibody that binds to the bischelate and a tumor antigen target, wherein the complex is configured to localize to a solid tumor expressing the tumor antigen target recognized by the bispecific antibody of the complex; (b) detecting radioactive levels emitted by the complex; and (c) selecting the subject for pretargeted radioimmunotherapy when the radioactive levels emitted by the complex are higher than a reference value. In some embodiments, the subject is human.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having cancer.

The cancer may be selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, and head-and-neck cancer. In some embodiments, the brain cancer is a pituitary adenoma, a meningioma, a neuroblastoma, or a craniopharyngioma.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally or intranasally. In certain embodiments, the complex is administered into the cerebral spinal fluid or blood of the subject.

In some embodiments of the methods disclosed herein, the radioactive levels emitted by the complex are detected between 4 to 24 hours after the complex is administered. In certain embodiments of the methods disclosed herein, the radioactive levels emitted by the complex are expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, *J Nucl Med.* 45(9):1431-4 (2004). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with cancer comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of Formula II to the subject, wherein the bischelate is configured to bind to the anti-DOTA bispecific antibody. In some embodiments, the subject is human. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the bischelate of Formula II is administered after a time period that may be sufficient to permit clearance of unbound anti-DOTA bispecific antibody.

The bischelate may be administered at any time between 1 minute to 4 or more days following administration of the anti-DOTA bispecific antibody. For example, in some embodiments, the bischelate is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the bischelate may be administered at any time after 4 or more days following administration of the anti-DOTA bispecific antibody.

Additionally or alternatively, in some embodiments, the method further comprises administering an effective amount of a clearing agent to the subject prior to administration of the bischelate. A clearing agent can be any molecule (dextran or dendrimer or polymer) that can be conjugated with C825-hapten. In some embodiments, the clearing agent is no more than 2000 kD, 1500 kD, 1000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, or 5 kD. In some embodiments, the clearing agent is a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.).

In some embodiments, the clearing agent and the bischelate of Formula II are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody (optionally so that relevant tumor cells are saturated); (ii) administration of a bischelate of Formula II and, optionally a clearing agent; (iii) optional additional administration of the bischelate of Formula II and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Additionally or alternatively, in some embodiments of the method, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM.

Additionally or alternatively, in some embodiments of the method, the anti-DOTA bispecific antibody and/or the bischelate is administered intravenously, intramuscularly, intraarterially, intrathecally, intracapsularly, intraorbitally, intradermally, intraperitoneally, transtracheally, subcutaneously, intracerebroventricularly, orally or intranasally.

In one aspect, the present disclosure provides a method for increasing tumor sensitivity to radiation therapy in a subject diagnosed with cancer comprising administering to the subject an effective amount of a complex comprising the bischelate of Formula II and a bispecific antibody that recognizes and binds to the bischelate and a tumor antigen target, wherein the complex is configured to localize to a tumor expressing the tumor antigen target recognized by the bispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments, the subject is human.

In another aspect, the present disclosure provides a method for treating cancer in a subject in need thereof comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of Formula II to the subject, wherein the bischelate is configured to bind to the anti-DOTA bispecific antibody. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the bischelate of Formula II is administered after a time period that may be sufficient to permit clearance of unbound anti-DOTA bispecific antibody. In some embodiments, the subject is human.

Accordingly, in some embodiments, the method further comprises administering an effective amount of a clearing agent to the subject prior to administration of the bischelate. The bischelate may be administered at any time between 1 minute to 4 or more days following administration of the anti-DOTA bispecific antibody. For example, in some embodiments, the bischelate is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the bischelate may be administered at any time after 4 or more days following administration of the anti-DOTA bispecific antibody.

The clearing agent may be a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.). In some embodiments, the clearing agent and the bischelate of Formula II are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody (optionally so that relevant tumor cells are saturated); (ii) administration of a bischelate of Formula II and, optionally a clearing agent; (iii) optional additional administration of the bischelate of Formula II and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Also provided herein are methods for treating cancer in a subject in need thereof comprising administering to the subject an effective amount of a complex comprising the bischelate of Formula II and a bispecific antibody that recognizes and binds to the bischelate and a tumor antigen target, wherein the complex is configured to localize to a tumor expressing the tumor antigen target recognized by the bispecific antibody of the complex. The therapeutic effectiveness of such a complex may be determined by computing the area under the curve (AUC) tumor: AUC normal tissue ratio. In some embodiments, the complex has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

The methods for treating cancer may further comprise sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11. In some embodiments, the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, and head-and-neck cancer. In some embodiments, the subject is human.

Kits

The present technology provides kits containing components suitable for treating or diagnosing cancer in a patient. In one aspect, the kits comprise a DOTA hapten of the present technology, at least one anti-DOTA BsAb, and instructions for use. The kits may further comprise a clearing agent (e.g., 500 kDa aminodextran conjugated to DOTA or 500 kD dextran-DOTA-Bn (Y)) and/or one or more radionuclides.

In some embodiments, the at least one anti-DOTA BsAb binds to a tumor antigen target selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), and Ki-67. Additionally or alternatively, in some embodiments, the at least one anti-DOTA BsAb binds to a tumor antigen target selected from the group consisting of CEACAM6, colon-specific antigen-p (CSAp), HLA-DR, CD40, CD74, CD138, EGFR, EGP-1, EGP-2, VEGF, PGF, insulin-like growth factor (LGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM. The at least one anti-DOTA BsAb may be provided in the form of a prefilled syringe or autoinjection pen containing a sterile, liquid formulation or lyophilized preparation of the antibody (e.g., Kivitz et al., Clin. Ther. 28:1619-29 (2006)).

Additionally or alternatively, in some embodiments of the kits of the present technology, the one or more radionuclides are selected from among $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Additionally or alternatively, in certain embodiments, the one or more radionuclides are selected from the group consisting of $^{86}$Y, $^{90}$Y, $^{89}$Sr, $^{165}$Dy, $^{186}$Re, $^{88}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, and $^{64}$Cu.

If the kit components are not formulated for oral administration, a device capable of delivering the kit components through some other route may be included. Examples of such devices include syringes (for parenteral administration) or inhalation devices.

The kit components may be packaged together or separated into two or more containers. In some embodiments, the containers may be vials that contain sterile, lyophilized formulations of a DOTA hapten and/or BsAb composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers.

EXAMPLES

Example 1: Materials and Methods for Generating the Compositions of the Present Technology General. DOTA-Bn-isothiocyanate (p-SCN-Bn-DOTA) was purchased from Macrocyclics, Inc. (Plano, Tex.) and Amine-PEG$_4$-DOTA was purchased from CheMatech (Dijon, France). Optima™ grade hydrochloric acid was purchased from Thermo Fisher Scientific (Waltham, Mass.). Chelex-100 resin, 200-400 mesh was purchased from Bio-Rad Laboratories (Hercules, Calif.). PD-10 gel-filtration size-exclusion columns (containing 8.3 mL of Sephadexm G-25 resin/column) were purchased from GE Healthcare Life Sciences (Pittsburgh, Pa.). All other reagents and synthesis-grade chemicals were purchased from Sigma-Aldrich (St. Louis, Mo.) and used without further purification. All solvents used for HPLC analysis (HPLC grade) and compound purification were also purchased from Thermo Fisher Scientific (Waltham, Mass.). All buffers and solutions were prepared using ultrapure water (18 MΩ-cm resistivity).

All liquid chromatography mass spectrometry (LC/MS) data was obtained using a Waters Autopure system (Milford, Mass.) comprising the following instrumentation: 2767 Sample Manager, 2545 Binary Gradient Module, System Fluidics Organizer, 2424 Evaporative Light Scattering Detector, 2998 Photodiode Array Detector, 3100 Mass Detector. HPLC solvents (solvent A, 0.05% TFA in water; solvent B, 0.05% TFA in acetonitrile) were filtered prior to use. The analytical method was 5-25% solvent B in 10 min, 1.2 mL/min flow rate. Analytical columns: Waters XBridge BEH300 (Milford, Mass.), C4, 3.5 µm, 4.6×50 mm and C18, 4 µm, 4.6×50 mm. Preparative method: 5-25% solvent B in 30 min, 20 mL/min flow rate. Preparative column: Waters XBridge Prep (Milford, Mass.) C18, 4 µm, Optimum Bed Density, 19×150 mm.

All NMR data were obtained with either a Bruker AV500 or AV600 instruments (Bruker, Billerica, Mass.) at ambient temperature. The following abbreviations were used: singlet (s), broad singlet (bs), doublet (d), triplet (t), quartet (q), pentet (p), doublet of a doublet (dd), multiplet (m).

All PET imaging experiments were conducted on a Focus 120 MicroPET camera (Siemens, Knoxville, Tenn.) dedicated small-animal scanner.

Figure 4:
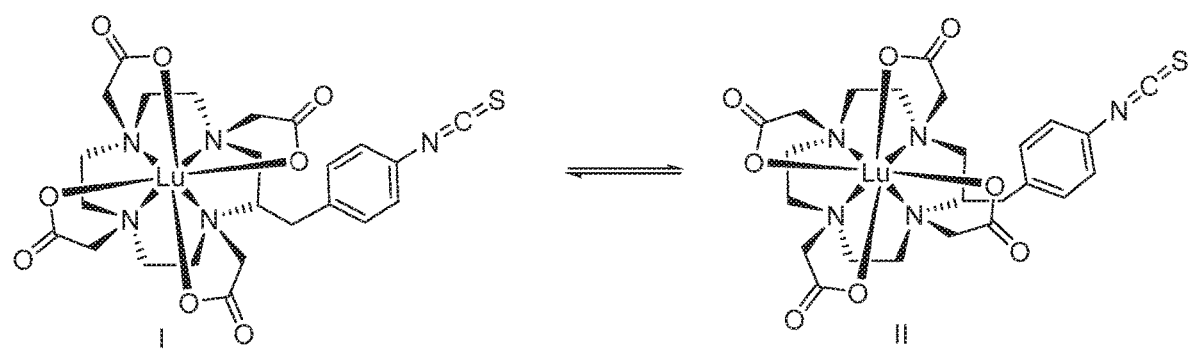
FIG. 4 shows interconversion between possible diastereoisomers of Lutetium-DOTA chelate.

Syntheses. Metal-loaded organic complexes such as DOTA complexes can sometimes exhibit isomerism (Aime et al., *Inorg Chem.* 36(10):2059-2068 (1997)). This phenomenon is present in Lutetium-DOTA complexes. As shown in FIG. 4, the two isolated isomers may be attributed to interconversion between square antiprismatic diastereoisomers of the complexes. The two Lutetium-DOTA isomers also exhibited differences in chromatographic and proton NMR data. In the experiments described herein, only the major isomer (which corresponds to structure I in FIG. 4) was assessed for biological activity.

Figure 5:
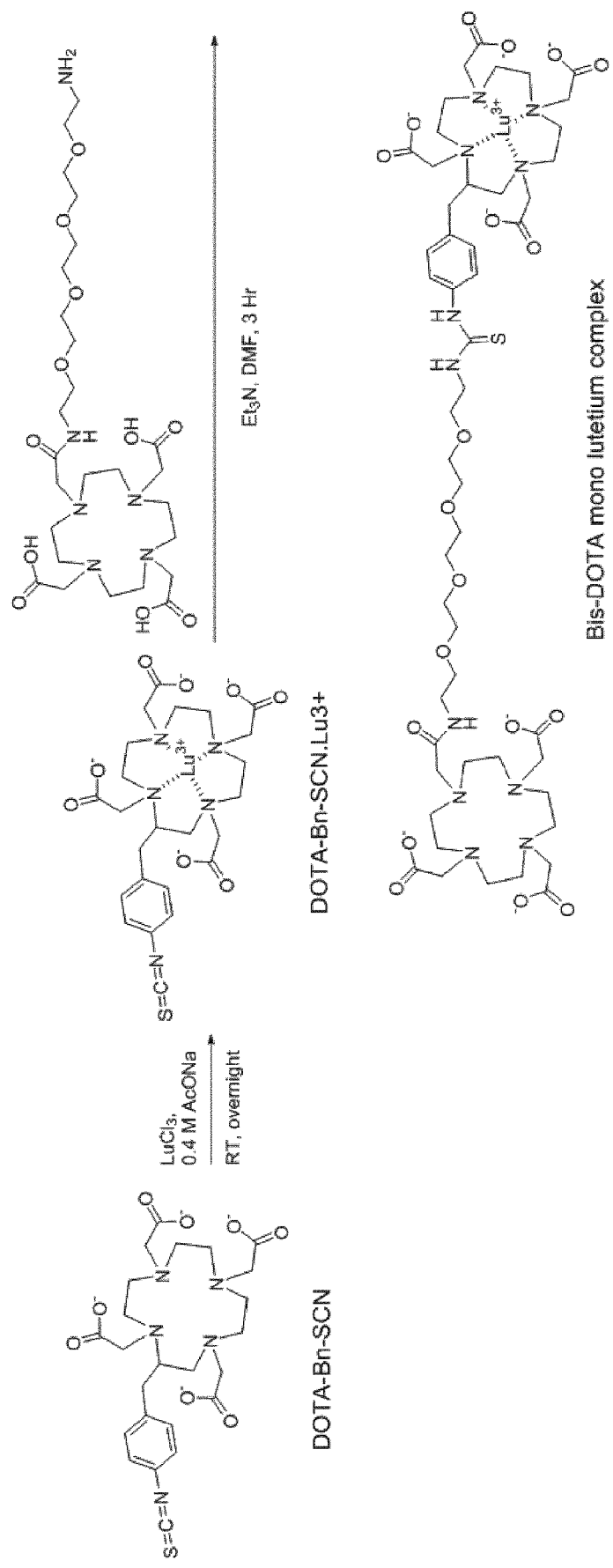
FIG. 5 shows the synthesis scheme of Bis-DOTA mono lutetium complex.

Synthesis of Bis-DOTA mono lutetium complex. DOTA-Bn-isothiocyanate was selected as a starting reagent for synthesis because of its relative stability during metal loading and subsequent purification and lyophilization. No attempts at optimization or recycling of possibly hydrolyzed isothiocyanate derivatives were made (FIG. 5). All experiments involving molecules with high metal complexing capacity such as DOTA were conducted in glassware that was pre-washed with metal-free HCl, rinsed with high purity water (e.g., glass-distilled water), and oven dried. Chromatography was carried out on manually packed glass columns to avoid loading the complexing agent with metal leached or extracted from metal column walls. The reverse phase purifications were carried out on clean, metal-free glass columns which were packed manually with loose C-18 silica gel. The water content in the final complexes was not measured.

Loading of Lutetium onto DOTA (p-SCN-Bn-DOTALu$^3$ complex formation). LuCl$_3$.6H$_2$O (127 mg, 326 μmol) was added to 0.4 mL of 0.4 M solution of sodium acetate. p-SCN-Bn-DOTA (45 mg, 65 μmol) was then introduced into the solution via syringe. The resulting mixture was stirred at room temperature overnight. Purification was performed with a reverse phase C-18 column using 0-40% acetonitrile in water as a gradient. Appropriate fractions were pooled and lyophilized to provide 18 mg (38% yield) of the desired complex as a white solid.

Bis-DOTA monocomplex of Lutetium (*Proteus*-DOTA). p-SCN-Bn-DOTA-Lu$^{3+}$ complex (18 mg, 24.9 μmol) and NH$_2$-PEG-4-DOTA (17 mg, 24.4 μmol) were added to anhydrous DMF (0.4 mL), followed by Et$_3$N (20 μL, 140 μmol). The mixture was stirred at room temperature for 3 hours. Solvent was removed under high vacuum, and residue was purified with a reverse phase C-18 column using 0-20% acetonitrile in water as a gradient to afford 2 isomers. The second eluting fraction was re-purified on a reverse phase C-18 column using 0-8% acetonitrile in water as a gradient. Appropriate fractions were pooled and lyophilized. First eluting isomer (2.1 mg, 6.4%), second isomer (11.2 mg, 34%) were isolated as triethyl ammonium salts (see FIG. 4).

First isomer: LC/MS m/z 1346.7 [calculated for C$_{50}$H$_{81}$LuN$_{11}$O$_{19}$S (M+H) 1346.5]. $^1$H NMR (600 MHz, D$_2$O, ppm), δ 7.25 (d, 2H, J=8.0 Hz), 7.19 (d, 2H, J=8.0 Hz), 3.75-3.21 (m, 55), 3.12-2.84 (m, 17H), 2.77-2.42 (m, 3H), 1.20 (t, 8H, J=7.3 Hz).

Second isomer: LC/MS m/z 1346.7 [calculated for C$_{50}$H$_{81}$LuN$_{11}$O$_{19}$S (M+H) 1346.5]. $^1$H NMR (600 MHz, D$_2$O, ppm), δ 7.24-7.20 (m, 4H), 3.75-3.00 (m, 57), 2.84-2.81 (m, 2H), 2.77-2.74 (m, 1H), 2.72-2.64 (m, 2H), 2.61-2.51 (m, 3H), 2.50-2.47 (m, 1H), 2.44-2.38 (m, 2H), 2.19 (m, 1H).

LC/MS: using 5-25% acetonitrile (ACN) (0.05% TFA)/water (0.05% TFA).

$^{225}$Ac-radiochemistry of *Proteus*-DOTA. Carrier free $^{222}$Ac (5.80×10$^4$ Ci/g) was obtained from Oak Ridge National Laboratory as a dried nitrate residue. The $^{222}$Ac nitrate was dissolved in 0.2 M Optima™ grade hydrochloric acid for subsequent radiochemistry. $^{225}$Ac-activity was measured using a CRC-15R radioisotope calibrator (Capintec, Inc., Florham Park, N.J.) set at 775 and the displayed activity value was multiplied by 5; samples were positioned at the bottom and center of the well for measurement. Water and buffers were rendered metal-free and sterile by passing them through a column of Chelex-100 resin, followed by filtration through a sterile-filer device (0.22- or 0.45-μM). Initially, *Proteus*-DOTA was suspended in water at 10 mg/mL and immediately transferred to a 1.8-mL Nunc vial, and any unused stock was promptly stored at −20° C. To prepare [$^{225}$Ac]*Proteus*-DOTA, 20 μL of carrier-free (5.80×10$^4$ Ci/g) actinium-225 nitrate (66 μCi) was mixed with 100 μL of 10 mg/mL *Proteus*-DOTA (1 mg; 0.741 μmoles) in a 1.8-mL Nunc vial. Next, 15 μL of L-ascorbic acid solution (150 g/L) and 100 μL of 3M ammonium acetate solution was added.

The pH of the solution was verified to be ~5.5 by spotting 1 μL of the reaction mixture onto Hydrion pH paper (range: 5.0-9.0). The reaction was incubated at 60° C. for 30 min, and then purified using a home-made ion-exchange column (Sephadex C-25 column) pre-equilibrated with 6 mL of normal sterile isotonic saline solution (NSS). The reaction mixture was added to the column and was eluted with 4 mL of NSS. Since 66.0 μCi was loaded and 62.0 μCi was obtained in the flow-through, a radiochemistry recovery yield of 94% was achieved. The final specific activity was 0.06 Ci/g or 84 Ci/mol.

$^{68}$Ga-radiochemistry of *Proteus*-DOTA. *Proteus*-DOTA was radiolabeled with gallium-68 ($^{68}$Ga) in order to study the pharmacokinetics of $^{68}$Ga *Proteus*-DOTA with dynamic positron-emission imaging of nude mice. $^{68}$Ga was eluted from the Australian Nuclear Science and Technology Organisation generator using 0.3 N HCl followed by concentration on ion exchange column (BioRad anion exchange column) using automatic elution controller system. The concentrated $^{68}$Ga was eluted from the ion exchange resin as [$^{68}$Ga]-K[Ga(OH)$_4$] using 0.5 M KOH solution in 600 μL volume. To neutralize and acidify the solution 25 μL of glacial acetic acid (>3 μL per 100 μL of 0.5 M KOH) was added to 500 μL eluate. The pH was <5 by pH paper. For $^{68}$Ga-radiochemistry of *Proteus*-DOTA, to an Eppendorf containing 10 pg of *Proteus*-DOTA (MW 1347, 7.4 nmoles of ligand) was added to 530 μL of neutralized [$^{68}$Ga]-K[Ga(OH)$_4$] and heated at 95° C. for 10 min. Following the radiolabeling incubation period, the reaction mixture containing the [$^{68}$Ga]*Proteus*-DOTA and a small amount of free $^{68}$Ga was drawn up through a Strata™-X cartridge (33 μm Polymeric Reversed Phase C-18 30 mg/l mL #8B-S100-TAK, Phenomenex® Inc., Torrance, Calif. USA) that was preconditioned by passing 1 mL of 95% ethanol (USP for injection) and 2.5 mL of pure water. The cartridge was then rinsed with 3 mL of water to remove any residual free $^{68}$Ga and finally the purified [$^{68}$Ga]*Proteus*-DOTA was eluted in 300 μL of ethanol (100%). Radiochemical purity was determined by radio HPLC which indicated >98% purity. HPLC was performed on a C-18 RP HPLC column (Phenomenex® Luna C-18, 5 μm 100 Å, 250×4.6 mm) using a gradient solvent system of 10-95% acetonitrile in 0.1% trifluoroacetic acid (TFA) from 3-10 min and at a flow rate of 1 mL/min. Under the conditions above, the pure product elutes as a broad peak with retention time of about 9.7 min. The final specific activity was about 2.7 mCi/7.4 nmol=365 mCi/μmol. When the reaction was repeated at a later date, the final specific activity was 1 mCi/7.4 nmol=135 mCi/μmol.

Cell Culture. The GPA33(+) human colorectal cancer (CRC) cell line SW1222 was obtained from the Ludwig Institute for Cancer Immunotherapy (New York, N.Y.) and expanded via serial passage. The HER2(+) breast cancer cell line BT-474, the HER2(+) gastric cancer cell line NCI-N87, and the GD2(+) neuroblastoma cell line IMR-32 were obtained from American Type Culture Collection (Manassas, Va.). SW1222 cells were cultured in Minimal Essential Medium supplemented with 10% heat-inactivated fetal calf serum, 2.0 mM glutamine, 100 units/mL penicillin, and 100 pg/mL streptomycin. BT-474 cells were cultured in Dulbecco's modified Eagle-high-glucose/F-12 medium supplemented with non-essential amino acids (0.1 mM), 10% heat-inactivated fetal calf serum, 100 units/mL of penicillin, and 100 pg/mL streptomycin. NCI-N87 and IMR-32 cells were cultured in RPMI media supplemented with 10% heat-inactivated fetal calf serum, 100 units/mL of penicillin, and 100 μg/mL streptomycin. All cells were maintained in a 37° C. environment containing 5% $CO_2$(g). Upon receipt of the cell line, cultures were established and cryopreserved in small aliquots to limit passages to less than three months, and were periodically tested for mycoplasma negativity using a commercial kit (Lonza, Basel, Switzerland). A solution of 0.25% trypsin/0.53 mM EDTA in Hanks Buffered Salt Solution without calcium and magnesium was used for trypsinization during cell passaging and harvesting.

Animal Care. For all intravenous injections, mice were gently warmed with a heat lamp and placed on a restrainer. The mice tails were sterilized with alcohol pads prior to carrying out the lateral tail vein injections. All animal experiments were done in accordance with protocols approved by the Institutional Animal Care and Use Committee of Memorial Sloan Kettering Cancer Center, which follows National Institutes of Health guidelines for animal welfare.

Animal Models. Athymic nu/nu female mice (6-8 weeks old; Harlan/Envigo) were allowed to acclimate in the vivarium for at least one week. For the BT-474 tumor model only, mice were implanted with estrogen (17β-estradiol; 0.72 mg/pellet 60-d release; Innovative Research of America) by trochar injection 3 days before inoculation with cells. For establishment of all tumors, groups of mice were inoculated with $5.0 \times 10^6$ cells in a 200 μL cell suspension of a 1:1 mixture of media with reconstituted basement membrane (BD Matrigel™, Collaborative Biomedical Products Inc., Bedford, Mass.) on lower flank via s.c. injection, and established tumors (100-300 $mm^3$) were observed within 7-10 days (SW1222) or 3-4 weeks (BT-474, NCI-N87, or IMR-32) using the formula for the volume of an ellipsoid.

Biodistribution Experiments. A treatment cycle of anti-GPA33 DOTA-PRIT consisted of three separate intravenous injections via the tail vein: 0.25 mg of huA33-C825 antibody (described in WO2016/130539) at t=−28 h, then 62.5 pg of clearing agent (500 kD-dextran-DOTA-Bn(Y)) at t=−4 h, and [$^{225}$Ac]*Proteus*-DOTA at t=0. For ex vivo biodistribution analysis following the radiohaptens or anti-HER2-C825/[$^{225}$Ac]*Proteus*-DOTA, mice were euthanized by $CO_2$ (g) asphyxiation, and the tumors and selected organs were harvested, rinsed with water, air-dried, weighed, and radio-assayed by gamma scintillation counting (Perkin Elmer Wallac Wizard 3", Perkin Elmer, Waltham, Mass.). Count rates were background- and decay-corrected, converted to activities using a system calibration factor specific for the isotope, normalized to the administered activity, and expressed as average percent injected dose per gram (% ID/g)±1 standard deviation. Differences in radioactivity concentration in tumor and various tissues were analyzed by Student's unpaired t test when appropriate.

In vitro Mixing of [$^{225}$Ac]*Proteus*-DOTA with a DOTA-PRIT BsAb, followed by In vivo Targeting Studies. [$^{225}$Ac]*Proteus*-DOTA was prepared to a final specific activity of 0.06 Ci/g or 84 Ci/mol. After one week of storage of [$^{225}$Ac]*Proteus*-DOTA at room temperature, an in vitro mixing experiment consisting of mixing 145 μL of 6.91 mg/mL of anti-HER2-C825 (4.8 nmol of BsAb or 9.6 nmol of C825) and 90 μL of [$^{225}$Ac]*Proteus*-DOTA (488 nCi/8.64 nmol) for 1 h at room temperature (final volume 235 μL). As a control, 1 mg of trastuzumab (6.67 nmol) with also mixed in vitro with 90 μL of [$^{225}$Ac]*Proteus*-DOTA (468 nCi/8.64 nmol) in the same manner as the anti-HER2-C825. These two solutions were run separately on PD-10 size-exclusion columns pre-equilibrated with saline+1% human serum albumin, and were compared with the column elution of 90 μL (488 nCi/8.64 nmol) of [$^{225}$Ac]*Proteus*-DOTA only. Elution fractions were counted on the gamma-counter using an open window setting.

PET Imaging and Biodistribution Studies with [$^8$Ga]*Proteus*-DOTA. [$^{68}$Ga]*Proteus*-DOTA was prepared to a final specific activity of about 2.7 mCi/7.4 nmol=365 mCi/μmol. Nude mice bearing HER2-expressing NCI-N87 human gastric carcinoma subcutaneous xenografts (n=4) were injected with 113-140 μCi (310-384 μmol) [$^{68}$Ga]*Proteus*-DOTA and imaged with dynamic positron-emission imaging for 15 minutes (min) post-injection (p.i.) (n=2), or with static imaging at 1 h p.i. (n=4). All animals were then sacrificed at 2 hours post injection for ex vivo biodistribution analysis. The list-mode data was histogrammed using the following protocol: 12×10 seconds, 6×30 seconds, 5×60 seconds, 4×300 seconds, 30 min, resulting in 24 total frames. Regions-of-interest were drawn around heart (for blood as cardiac outflow) and kidney to determine activity concentrations (as % ID/g).

Biodistribution Studies Following In vivo Targeting with Anti-GPA33-DOTA-PRIT+[$^{225}$Ac]*Proteus*-DOTA. [$^{225}$Ac]*Proteus*-DOTA was prepared to a final specific activity of 0.20 Ci/g or 274 Ci/mol and injected into groups of animals within 24-48 hours of preparation. Animals that had received injections of huA33-C825 and clearing agent were injected with 182 μmol/50 nCi of [$^{225}$Ac]*Proteus*-DOTA that was prepared approximately 24 hours prior. The following day, animals were sacrificed for ex vivo biodistribution assessment at 24 hours post injection of [$^{225}$Ac]*Proteus*-DOTA in tumors and select normal tissues. A control group of non-tumor bearing animals were injected with 198 μmol/50 nCi of [$^{225}$Ac]*Proteus*-DOTA that was prepared approximately 48 hours prior, and were sacrificed 1 hour post injection of [$^{225}$Ac]*Proteus*-DOTA for ex vivo biodistribution assessment in normal tissues. Carcass radioactivity was not collected during this study.

Preparation of [$^{111}$In]*Proteus*-DOTA. Using similar radiochemical methods, [$^{111}$In]*Proteus*-DOTA was prepared from [$^{111}$In]indium chloride (Nuclear Diagnostic Products, Inc., Rockaway, N.J.; 249 MBq [6.73 mCi]) and 150 μL of 10 mg/mL *Proteus*-DOTA (1.5 mg; 1.11 μmoles). The [$^{111}$In]*Proteus*-DOTA yield was >98% and the final Specific Activity was 162.8 GBq/g [4.4 Ci/g] or 2.28 E5 GBq/mol [6160

Ci/mol]. This preparation was used for pharmacokinetic studies. Prior to administration into mice, the [$^{111}$In]*Proteus*-DOTA was purified using a Strata™-X cartridge (33 μm Polymeric Reversed Phase C-18 30 mg/l mL #8B-S100-TAK, Phenomenex® Inc., Torrance, Calif. USA) as described for [$^{68}$Ga]*Proteus*-DOTA and the radiochemical purity was verified to be >98% either using an in vitro binding assay with excess BsAb or by analytical reverse-phase HPLC coupled with radiodetection.

Example 2: In Vitro Studies with the Compositions of the Present Technology

This Example demonstrates that the compositions of the present technology are useful for pretargeted radioimmunotherapy.

Figure 1:
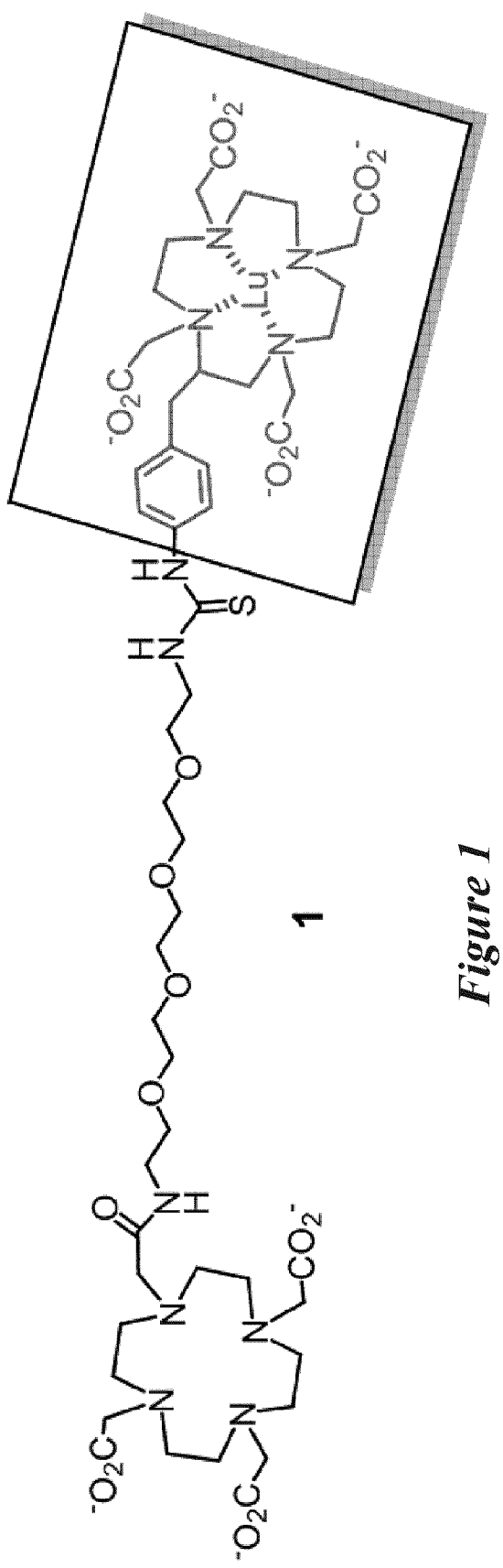
FIG. 1 shows the structure of the DOTA-hapten of the present technology (a.k.a., Proteus-DOTA) (chemical formula: $C_{50}H_{80}LuN_{11}O_{19}S^{3-}$; exact mass: 1345.48; molecular weight: 1346.28). The boxed portion of the molecule is a non-radioactive benzyl-DOTA (Lu) hapten that is recognized by the anti-DOTA-hapten antibody single chain variable fragment C825 at a $K_d$=10 pM. The empty three-arm DOTA portion of the molecule can accommodate a variety of radiometals relevant to therapy and/or imaging including $^{225}$Ac, $^{68}$Ga, and $^{64}$Cu.

*Proteus*-DOTA contains a 3-arm DOTA chelating agent (that efficiently forms stable complexes with $^{225}$Ac), attached to a benzyl-DOTA-Lu complex separated by a PEG linker. See FIG. 1. *Proteus*-DOTA was synthesized by mixing two bifunctional DOTA chelators: commercial 2,2', 2"-(10-(17-amino-2-oxo-6,9,12,15-tetraoxa-3-azaheptadecyl)-1,4,7,10-tetraazacyclododecane-1,4,7-triyl)triacetic acid (amine-PEG$_4$-DOTA) and the non-radioactive lutetium-complex of 2-(4-isothiocyanatobenzyl)-1,4,7,10-tetraazacyclododecane-tetraacetic acid (p-SCN-Bn-DOTA Lu$^{3+}$ complex) prepared from commercial p-SCN-Bn-DOTA and LuCl$_3$.6H$_2$O. Using semi-preparative C-18 high-pressure liquid chromatography, *Proteus*-DOTA was prepared in very high purity (>98%) and with an overall yield of 34%.

Radiochemistry of *Proteus*-DOTA was accomplished using carrier free $^{225}$Ac (5.80×104 Ci/g) as a dried nitrate residue. The $^{225}$Ac-labeled *Proteus*-DOTA ([$^{225}$Ac]*Proteus*-DOTA) (n=3) was obtained in 94-100% radiochemical yield in high purity and with a specific activity between 84 and 274 Ci/mol, suggesting that the Bn-DOTA-Lu moiety of *Proteus*-DOTA does not interfere with $^{225}$Ac-radiometal complexation by the 3-arm DOTA chelator moiety.

Figure 6:
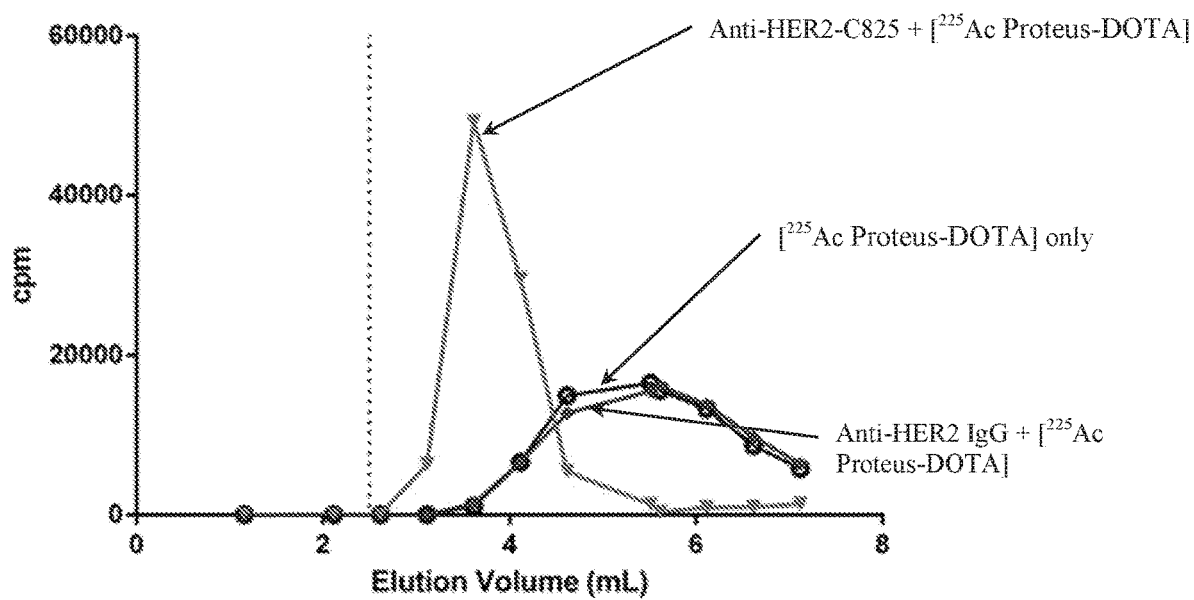
FIG. 6 shows the in vitro mixing of anti-HER2-C825 or anti-HER2 IgG with [$^{225}$Ac Proteus-DOTA], followed by size-exclusion chromatography. The dotted line indicates the void volume as specified by the column manufacturer. Purified [$^{225}$Ac Proteus-DOTA] hapten was used as a reference.

FIG. 6 shows that the binding of a DOTA-PRIT BsAb (anti-HER2-C825) with [$^{225}$Ac]*Proteus*-DOTA was demonstrated using in vitro mixing studies followed by size-exclusion chromatography (SEC) to separate the high-molecular weight BsAb/[$^{225}$Ac]*Proteus*-DOTA complex (~212 kD) from free [$^{225}$Ac]*Proteus*-DOTA (~1.5 kD). This was done by mixing the BsAb (~210 kD) in slight molar excess to [$^{225}$Ac]*Proteus*-DOTA (9.6 nmol of C825/8.6 nmol of [$^{225}$Ac]*Proteus*-DOTA), followed by incubation at room temperature for 1 hour. In order to show that the complex formation was dependent on the presence of the C825 scFv, control studies were done in parallel either with the corresponding parent IgG (150 kD) to the BsAb (IgG+[$^{225}$Ac]*Proteus*-DOTA) or with [$^{225}$Ac]*Proteus*-DOTA alone.

As shown in FIG. 6, there was a clear difference in the elution profile of BsAb+[$^{225}$Ac]*Proteus*-DOTA, with 89% of the recovered $^{225}$Ac-activity eluting within the first 4.1 mL, presumably as the BsAb/[$^{225}$Ac]*Proteus*-DOTA complex. In comparison, the controls (IgG+[$^{225}$Ac]*Proteus*-DOTA or [225Ac]*Proteus*-DOTA) showed 9.7% and 9.3% $^{225}$Ac-activity eluting within the first 4.1 mL, respectively, while the remaining activity (90%) was recovered in the elution fractions collected between 4.6-7.1 mL of elution volume.

These results demonstrate that (a) the geometry of the *Proteus*-DOTA haptens of the present technology does not negatively impact the recognition and binding activities of a DOTA-BsAb and (b) the presence of non-radioactive lutetium in the *Proteus*-DOTA haptens of the present technology does not interfere with $^{225}$Ac radiochemistry. Accordingly, the compositions disclosed herein are useful in pretargeted radioimmunotherapy methods.

Example 3: In Vivo Studies with the Compositions of the Present Technology

This Example demonstrates that the compositions of the present technology are useful for in vivo diagnostic imaging methods and pretargeted radioimmunotherapy.

To determine whether isolated BsAb/[$^{225}$Ac]*Proteus*-DOTA complexes could target tumors in vivo, a biodistribution assay was conducted after SEC purification with two groups of athymic nude mice (n=3) bearing subcutaneous HER2-expressing BT-474 xenografts. The two BsAb/[$^{225}$Ac]*Proteus*-DOTA fractions containing the most radioactivity (fractions 5 and 6, corresponding to elutions 3.1-3.6 mL and 3.6 to 4.1 mL, respectively; 83% of total recovered activity) were combined (total volume: 1 mL) and groups of xenograft-bearing mice were intravenously injected in the lateral tail vein with either: 250 μL of PD10-purified anti-HER2-C825/[$^{225}$Ac]*Proteus*-DOTA solution (1.0 nmol of anti-HER2-C825/mouse; 3.7 kBq [100 nCi]) or [$^{225}$Ac]*Proteus*-DOTA (0.51 nmol, 1.1 kBq [30 nCi]) formulated in a total volume of 250 μL and were sacrificed 4 h post-injection for ex vivo biodistribution assessment.

Figure 2:
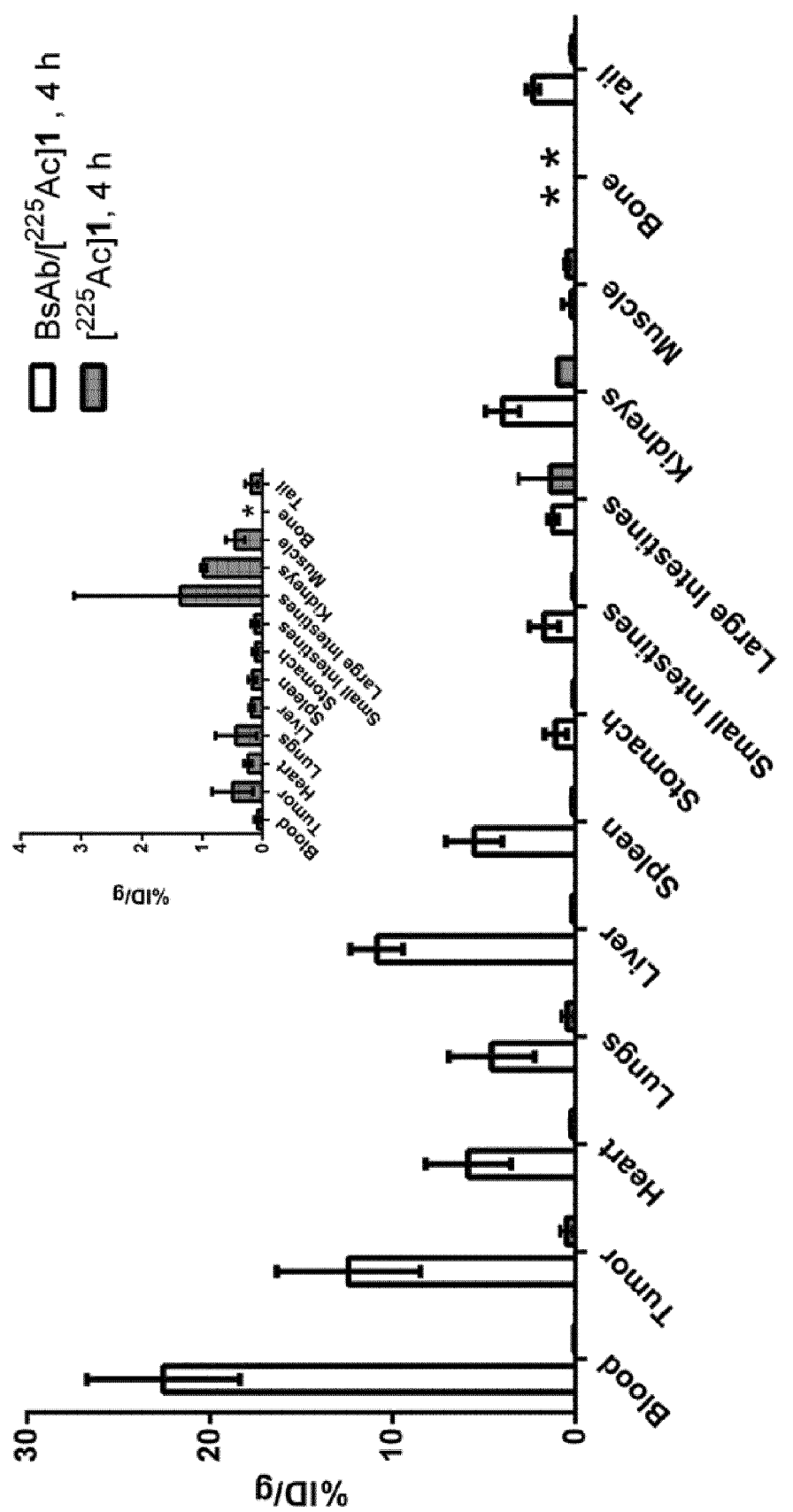
FIG. 2 shows the biodistribution of either the bispecific antibody (BsAb) anti-HER2-C825 complexed with [$^{225}$Ac Proteus-DOTA] or the [$^{225}$Ac Proteus-DOTA] hapten alone in tumor-bearing athymic nude mice. The $^{225}$Ac-Proteus-DOTA haptens were injected intravenously via the lateral tail vein and euthanized 4 hours later for organ collection and radioactivity assessment. Asterisk (*) indicates levels below the limit of detection. Two groups of nude mice with subcutaneous BT474 tumors (3 mice each) were treated with either: [$^{225}$Ac Proteus-DOTA] only (0.51 nmol/mouse; ~30 nCi of $^{225}$Ac/mouse) or PD10-purified [anti-HER2-C825/ [$^{225}$Ac Proteus-DOTA] complex (estimate 1.79 nmol of $^{225}$Ac Proteus-DOTA/mouse, 1.0 nmol of antibody/mouse; 100 nCi $^{225}$Ac/mouse), and sacrificed 4 h post-injection for ex vivo biodistribution assay. The tissue samples were read in the gamma counter the following day at equilibrium.

FIG. 2 shows that anti-HER2-C825/[$^{225}$Ac]*Proteus*-DOTA was able to target tumors in vivo, while [$^{225}$Ac]*Proteus*-DOTA showed negligible tumor accumulation (12.4±3.92% injected dose per gram (% ID/g) or 0.50±0.34% ID/g, respectively) at 4 h after injection. Further, all assayed tissues showed an uptake of ≤~2% ID/g for [$^{225}$Ac]*Proteus*-DOTA suggesting renal elimination and minimal retention in tissues. The blood activity of anti-HER2-C825 BsAb/[$^{225}$Ac]*Proteus*-DOTA was greater than tumor (22.6±4.18% ID/g) at 4 hours after injection, suggesting that the BsAb/[$^5$Ac]*Proteus*-DOTA was relatively stable in plasma and could have potentially resulted in further tumor accumulation if the animals were euthanized at a later time point.

Figure 7:
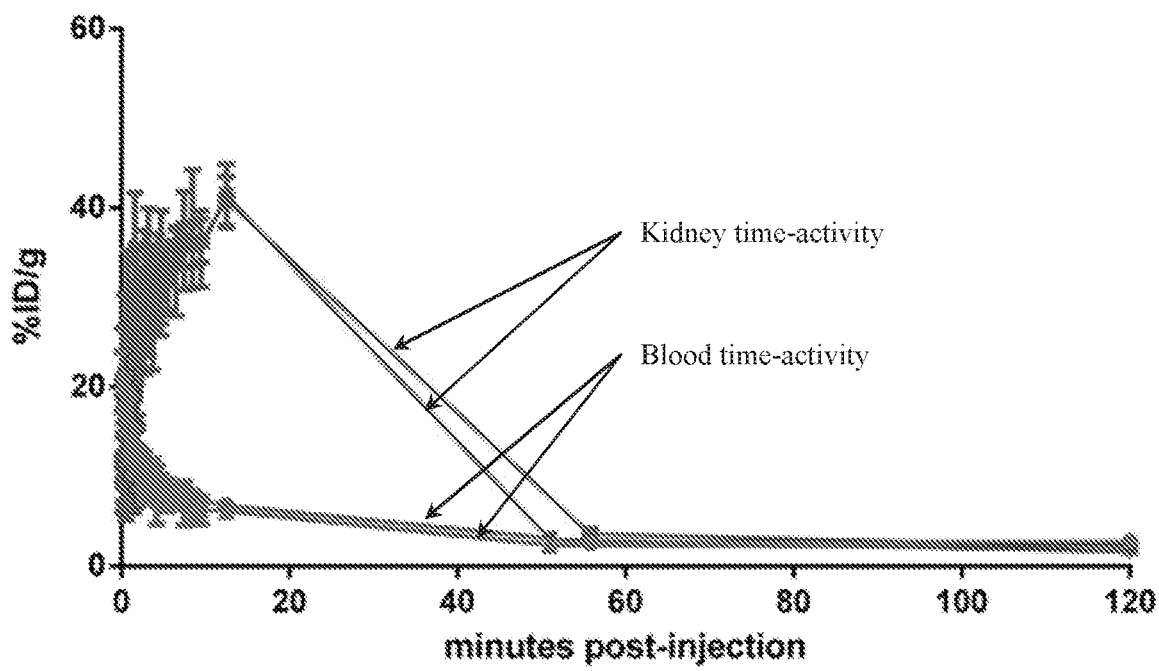
FIG. 7 shows the dynamic PET (0-15 min p.i.), static PET (51 or 56 min p.i.), and ex vivo biodistribution data (2 h p.i.) from nude mice bearing NCI-N87 tumors administered [$^{68}$Ga-Proteus-DOTA] s.c. at t=0 min. Decay-corrected blood and kidney time-activity curves (TAC) are shown for two individual mice. The blood-TAC for each of the animals was separately curve-fitted to a non-linear two phase decay equation. The (i) percent fast, (ii) half life (slow; minutes), (iii) half-life (fast; minutes), and (iv) $R^2$ values for mouse 1/mouse 2 were: 46/56, 13.2/13.7, 1.4/0.94, and 0.95/0.99, respectively.

The blood half-life of *Proteus*-DOTA was further investigated by injecting mice bearing NCI-N87 tumors with a PET imaging surrogate, [$^{68}$Ga]*Proteus*-DOTA. Using a combination of dynamic PET imaging and biodistribution studies, the percent fast, half life (slow; minutes), half-life (fast; minutes), and R$^2$ values for mouse 1/mouse 2 were calculated to be: 46/56, 13.2/13.7, 1.4/0.94, and 0.95/0.99, respectively. FIG. 7 and Table 1 show rapid renal elimination as evidenced by the high kidney uptake followed by rapid clearance.

TABLE 1

| Organ | [$^{68}$Ga] Proteus-DOTA (n = 4) 2 h p.i. |
|---|---|
| Blood | 2.29 ± 0.31 |
| Tumor | 0.65 ± 0.08 |
| Heart | 0.75 ± 0.10 |
| Lungs | 1.00 ± 0.13 |
| Liver | 1.19 ± 0.08 |
| Spleen | 0.56 ± 0.13 |
| Stomach | 0.19 ± 0.05 |
| Small Intestine | 0.59 ± 0.21 |
| Large Intestine | 0.44 ± 0.10 |
| Kidneys | 1.53 ± 0.50 |
| Muscle | 0.17 ± 0.03 |
| Bone | 0.39 ± 0.07 |

To demonstrate that radiolabeled *Proteus*-DOTA could be used for DOTA-PRIT, a group of athymic nude mice bearing GPA33-expressing SW1222 xenografts was injected with the BsAb huA33-C825 (1.19 nmol) and a clearing agent either 28 hours or 4 hours prior to administration of [$^{225}$Ac]*Proteus*-DOTA (182 pmol, 1.85 kBq [50 nCi]). A control group of healthy nude mice were injected with [$^{225}$Ac]*Proteus*-DOTA only (198 pmol, 1.85 kBq [50 nCi]) to evaluate normal tissue uptake of the [$^{225}$Ac]*Proteus*-DOTA preparation.

Figure 3:
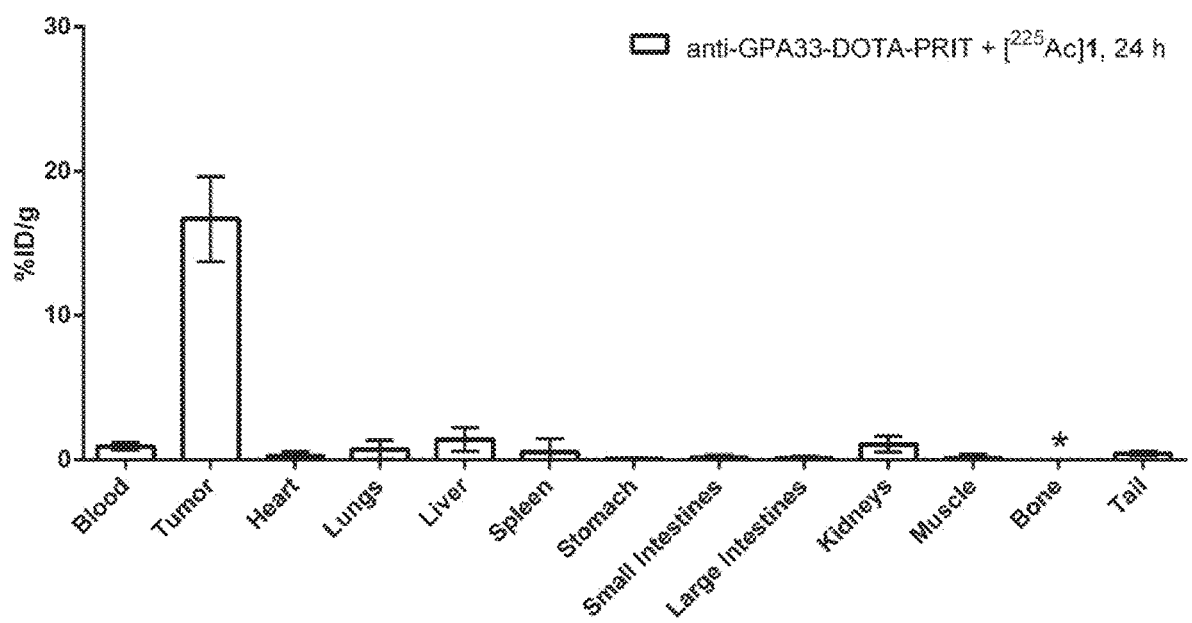
FIG. 3 shows the biodistribution of pretargeted [$^{225}$Ac Proteus-DOTA] hapten in tumor-bearing athymic nude mice. Following intravenous injections (via the lateral tail vein) of huGPA33-C825 BsAb, a clearing agent and [$^{225}$Ac Proteus-DOTA] hapten, the animals were euthanized 24 hours later for organ collection and radioactivity assessment. Asterisk (*) indicates levels below the limit of detection.

The mice undergoing PRIT were sacrificed 24 hours after injection of [$^{225}$Ac]*Proteus*-DOTA, while those given only [$^{225}$Ac]*Proteus*-DOTA were sacrificed 1 hour after injection for biodistribution assessment. As shown in Table 2 and FIG. 3, animals undergoing PRIT with BsAb huA33-C825, the blood, tumor, and kidney uptakes at 24 h after injection were 0.94±0.26% ID/g, 16.71±2.95% ID/g, and 1.08±0.55% ID/g, respectively, corresponding to tumor-to-organ activity ratios of about 18:1 and 16:1 for blood and kidney, respectively. The blood and kidney uptake of [$^{225}$Ac]*Proteus*-DOTA alone was 0.31±0.54% ID/g and 0.63±0.41% ID/g at 1 h after injection, indicating rapid renal clearance and negligible normal tissue uptake.

TABLE 2

| Organ | Pretargeted [$^{225}$Ac] Proteus-DOTA (n = 3) 24 h p.i. | [$^{225}$Ac] Proteus-DOTA alone (n = 3) 1 h p.i. |
|---|---|---|
| Blood | 0.94 ± 0.26$^a$ | 0.31 ± 0.54 |
| SW1222 tumor | 16.71 ± 2.95 | N/A |
| Heart | 0.28 ± 0.28 | $^b$ |
| Lungs | 0.70 ± 0.67 | $^b$ |
| Liver | 1.40 ± 0.82 | 0.01 ± 0.02 |
| Spleen | 0.54 ± 0.93 | 0.04 ± 0.06 |
| Stomach | 0.07 ± 0.08 | 0.24 ± 0.38 |
| Small Intestine | 0.16 ± 0.18 | 0.16 ± 0.26 |
| Large Intestine | 0.11 ± 0.12 | 0.02 ± 0.02 |
| Kidneys | 1.08 ± 0.55 | 0.63 ± 0.41 |
| Muscle | 0.13 ± 0.23 | 0.98 ± 0.91 |
| Bone | 0.00 ± 0.00 | 0.45 ± 0.79 |
| Tumor-to-tissue ratios | | |
| Blood | 17.9 ± 4.0 | |
| Heart | 60.4 ± 35.8 | |
| Lungs | 24.0 ± 13.5 | |
| Liver | 11.9 ± 4.2 | |
| Spleen | 31.1 ± 31.3 | |
| Stomach | 238.8 ± 150.7 | |
| Small Intestine | 102.3 ± 67.1 | |
| Large Intestine | 147.5 ± 90.9 | |
| Kidneys | 15.5 ± 4.8 | |
| Muscle | 128.6 ± 129.2 | |
| Bone | N/A | |

The high degree of tumor penetration observed during DOTA-PRIT with the *Proteus*-DOTA haptens of the present technology is significant because not all DOTA haptens are equally effective in promoting tumor accumulation during PRIT. For example, pretargeting with $^{225}$Ac-DOTA-Bn in vivo using a model PRIT system led to unremarkable tumor uptake of $^{225}$Ac-DOTA-Bn 24 hours post-injection (<1% ID/g). See FIG. 8.

These results demonstrate that (a) the geometry of the *Proteus*-DOTA haptens of the present technology does not impair the recognition and binding activities of a DOTA-BsAb (i.e., the DOTA-BsAbs can effectively bind both the radiolabeled *Proteus*-DOTA hapten and the tumor antigen target, e.g., GPA33 or HER2), (b) the presence of non-radioactive lutetium in the *Proteus*-DOTA haptens of the present technology does not interfere with $^{225}$Ac radiochemistry and (c) the *Proteus*-DOTA haptens of the present technology can be used to generate radiolabeled-BsAb complexes that retain tumor binding in vivo, and/or are useful for in vivo pretargeting with DOTA-PRIT. Accordingly, the compositions of the present technology are useful for in vivo diagnostic imaging methods and pretargeted radioimmunotherapy.

Figure 9A:
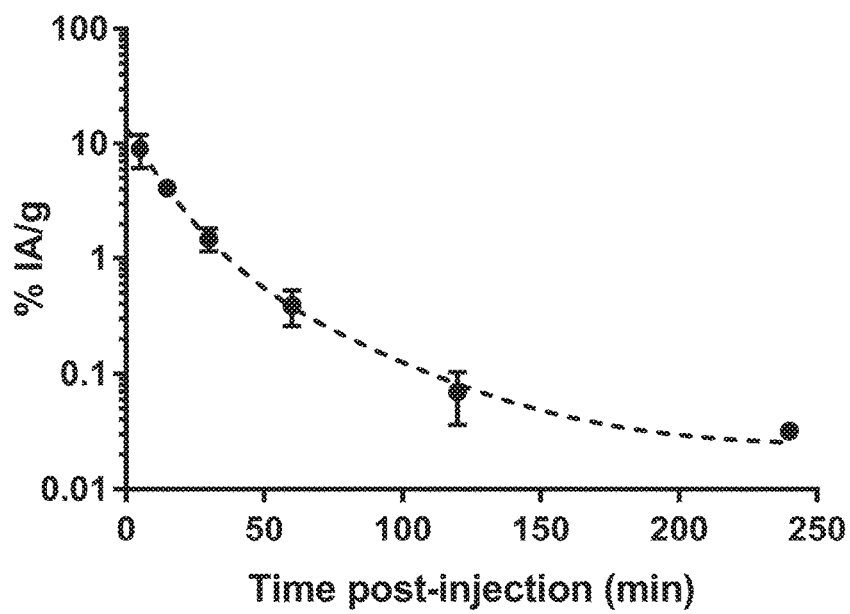
FIG. 9(A) shows the in vivo biodistribution and pharmacokinetics of radiolabeled Proteus-DOTA in tumor-free nude mice. The blood half-life of surrogate [$^{111}$In] Proteus-DOTA was determined. Dotted line indicates nonlinear two phase decay analysis used to calculate half-life ($R^2$=0.913). Data is presented as mean ±SD.
Figure 9B:
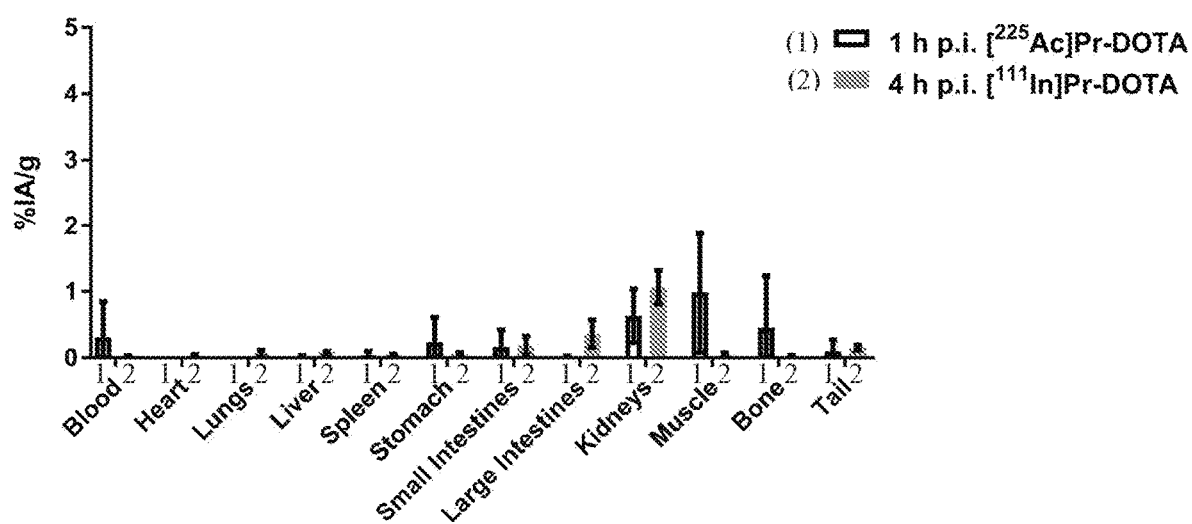
FIG. 9(B) shows the in vivo biodistribution and pharmacokinetics of radiolabeled Proteus-DOTA in tumor-free nude mice. The radiolabeled Proteus-DOTA tracers were injected i.v. via the lateral tail vein into groups of mice and euthanized 1-4 h later for organ collection and assay of radioactivity. Data is presented as mean ±SD.

Example 4: In Vivo Biodistribution, Clearance, and Toxicity Profiles of the Compositions of the Present Technology In initial experiments with tumor-free nude mice using [$^{111}$In]*Proteus*-DOTA as a surrogate for [$^{225}$Ac]*Proteus*-DOTA, the blood half-life of [$^{111}$In]*Proteus*-DOTA was determined to be biphasic, with half-lives of 7.49 minutes (alpha; 87.7%) and 24.8 minutes (beta) ($R^2$=0.913) (FIG. 9(A)). A biodistribution assay conducted at 240 min p.i. (4 h) of tracer showed very little uptake in normal tissues (as percent injected activity per gram of tissue; % IA/g), including low kidney retention (0.96±0.25; n=5; mean ±SD). See FIG. 9(B). After tissue dissection, the carcass was assayed in the dose-calibrator to determine remaining $^{111}$In-activity (0.952±0.162% ID; n=5; mean ±SD). See FIG. 12.

During a biodistribution study of [$^{225}$Ac]*Proteus*-DOTA in tumor-free nude mice, the blood, liver, and kidney uptake of [$^{225}$Ac]*Proteus*-DOTA was 0.31±0.54, 0.04±0.06, and 0.63±0.41% ID/g at 1 h after injection, indicating acceptable in vivo stability and negligible kidney retention. See FIG. 9(B).

Figure 10:
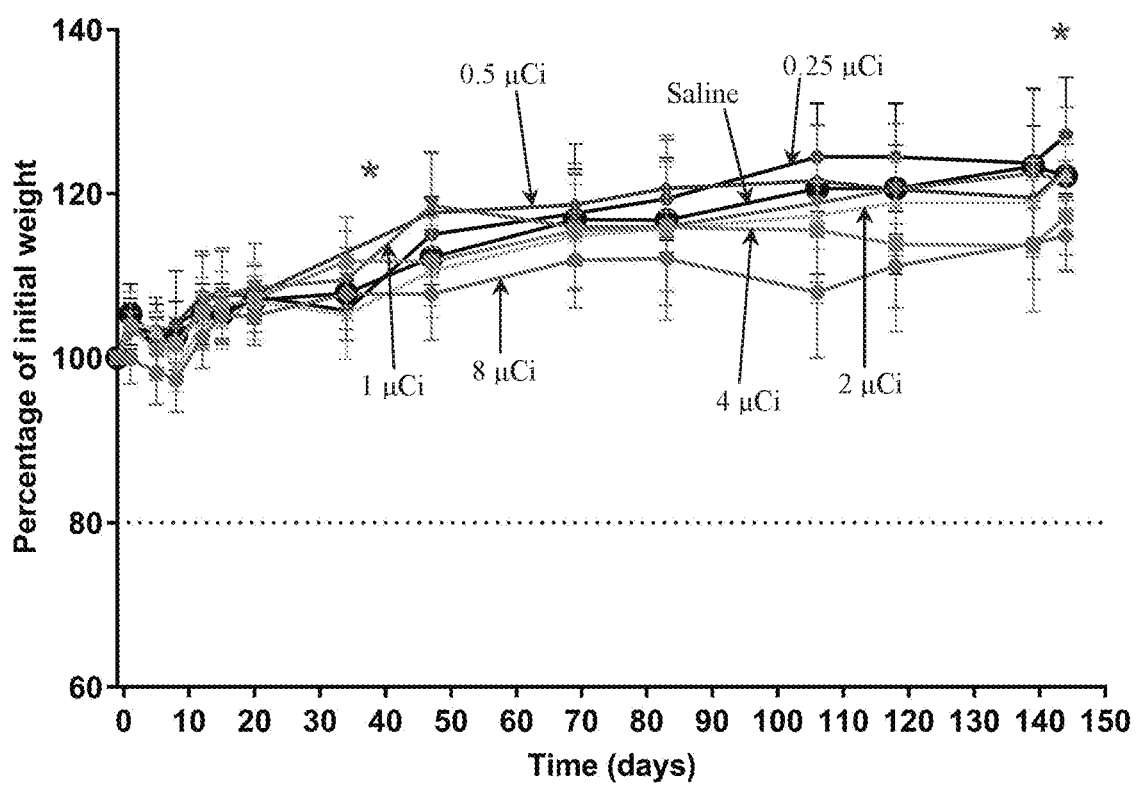
FIG. 10 shows a toxicology study of escalating doses of [$^{225}$Ac]Proteus-DOTA in healthy nude mice. The maximum tolerated dose was not reached. Treated animal weights plotted as the percentage of pre-treatment baseline weight.

Toxicology study of [$^{225}$Ac]Pr-DOTA in healthy mice. A dose-escalation toxicity study was performed to evaluate any morbidity and histopathological damage attributed to [$^{225}$Ac]*Proteus*-DOTA. Groups of tumor-free nude mice were treated with a single bolus i.v. injection of varying dose levels of [$^{225}$Ac]*Proteus*-DOTA (0, 0.25, 0.5, 1, 2, 4, or 8 μCi/mouse; n=5 per dose level) and monitored daily and weighed up to twice weekly for evidence of treatment induced toxicity for 145 days post-injection. Unscheduled mortality (mice found dead or found sick and euthanized) were submitted for pathology. In summary, no toxicity was observed (as defined as >10% weight loss; FIG. 10), and no radiation-induced histologic organ damage (e.g., kidney degeneration) was observed at any dose level at necropsy performed at 145 days. No significant group differences were observed in organ weights (e.g., no shrinkage of kidney, liver, or spleen; FIG. 11). A total of three unscheduled mortalities occurred: 2/5 from the 0.5 μCi dose group; one on day 36 that was submitted for necropsy because of 20% weight loss-no gross pathologic or histopathologic lesions were observed, and no significant findings were observed on hematology and serum chemistry; and by the time the other mouse was found dead on day 144, necropsy was not possible. In addition, one mouse from group 8 μCi was euthanized after 123 days with a *Staphylococcus* bacterial infection. The significant findings in this mouse were histiocytic and eosinophilic myocardis, eosinophilic interstitial pneumonia, soft tissue hemorrhages, marked thrombocytopenia, and mild anemia with elevation of reticulocytes. The myocarditis, pnemonia, and mild anemia were related to some findings observed at scheduled sacrifice. Such thrombocytopenia with secondary hemorrhages was not observed in other mice in this study. Serum chemistry was unremarkable.

One histopathologic lesion that appeared to be related to the administration of [$^{225}$Ac]*Proteus*-DOTA was histiocytic and eosinophilic inflammation in some organs. These were inflammatory lesions composed predominantly of eosinophils and macrophages affecting multiple organs (although each affected mouse usually had lesions in only 1 or 2 of these organs): heart, lungs, kidneys, spleen, liver, urinary bladder. There was an apparent dose-response (3/5 mice affected in 8 Ci group, 1/5 in 4 µCi, 1/5 in 2 µCi, 0/5 in 1 µCi, 0/4 in 0.5 µCi, 0/5 in 0.25 µCi). Similar lesions were observed during a toxicity study 100-200 days following treatment of mice with DOTA-PRIT+$^{177}$Lu-DOTA-Bn (Cheal, S. M. et al., *J Nucl Med* 58, 1735-1742 (2017)). Based on blood counts, a mild (~10%) decrease of red blood cells mass was observed in the highest dose group (8 µCi), but not associated with any clinical signs or symptoms. No effect of [$^{225}$Ac]*Proteus*-DOTA was observed on serum chemistry at any dose level (n=29).

These results demonstrate that [$^{225}$Ac]*Proteus*-DOTA was nontoxic, with no acute or chronic radiation damage to normal tissues such as marrow, liver, or kidney observed at doses as high as 8 µCi (296 kBq)/mouse. These data suggest that $^{225}$Ac biproducts, $^{22}$Fr and $^{213}$Bi, likely did not accumulate appreciably in kidneys, as long-term renal toxicity has been reported (e.g., glomerular loss at 160 kBq dose of [$^{225}$Ac]DOTA-c(RGDyK)$^6$ at 16 weeks; collapse of cortical tissue due to loss of tubular epithelium in the kidney cortex at 14.8 kBq dose of $^{225}$Ac-labeled anti-rat HER-2/neu monoclonal antibody at 1 year; see Song, H. et al., *Cancer research* 69, 8941-8948 (2009)).

Efficient and specific tumor targeting of [$^{225}$Ac]*Proteus*-DOTA. Preliminary experiments showed retention of BsAb binding avidity for antigen and for the Lu-DOTA moiety of [$^{225}$Ac]*Proteus*-DOTA. In order to demonstrate that [$^{225}$Ac]*Proteus*-DOTA could be used in combination with DOTA-PRIT for efficient tumor targeting in vivo, a group of nude mice bearing GPA33-expressing SW1222 xenografts was injected i.v. with the BsAb huA33-C825 (250 µg; 1.19 nmol) 28 h prior and i.v. with a clearing agent (62.5µg; 0.125 nmol dextran; 7.625 nmol (Y)DOTA) 4 h prior to administration of [$^{225}$Ac]*Proteus*-DOTA (182 pmol, 1.85 kBq [50 nCi]). These mice were sacrificed 24 h p.i. of [$^{225}$Ac]*Proteus*-DOTA for biodistribution assay. All animals were sacrificed at 24 h p.i. for biodistribution. For those animals undergoing pretargeted radioimmunotherapy with [$^{225}$Ac]*Proteus*-DOTA, the blood, tumor, and kidney uptakes (as percent injected activity per gram of tissue; % IA/g) at 24 h p.i. were 0.94±0.26, 16.71±2.95, and 1.08±0.55, respectively, corresponding to tumor-to-organ activity ratios of about 18:1 and 16:1 for blood and kidney, respectively. The liver uptake as percent injected activity per gram of tissue; % IA/g) at 24 h p.i. were 1.40±0.47 and bone update was undetectable. These tumor-to-organ activity ratios are similar to previous biodistribution studies carried out with anti-GPA33-DOTA-PRIT using tracer $^{177}$Lu-DOTA-Bn or $^{86}$Y-DOTA-Bn in the same animal model, where mean tumor uptakes for both DOTA-haptens were ~8% ID/g ((1.85-8.8 MBq; 10-50 pmol for either M-DOTA-Bn haptens) (see Cheal, S. M. et al., *Eur J Nucl Med Mol Imaging* 43, 925-937 (2016)) at 24 hours p.i., suggesting that the affinity of C825 for [$^{225}$Ac]*Proteus*-DOTA was similar.

In addition to studies with tracer doses of radiolabeled *Proteus*-DOTA, the upper limit for absolute tumor uptake of radiolabeled *Proteus*-DOTA was determined using in vivo competition studies. Biodistribution experiments were conducted 24 h following dosing of groups of tumor bearing mice with wide mass range of *Proteus*-DOTA spanning 2 orders of magnitude (~170-33800 pmol), showing maximum tumor uptake ("Bmax") of ~60 pmol DOTA-hapten/gram of SW1222 tumor. These results are comparable to that achieved with pretargeted $^{177}$Lu-DOTA-Bn in the same system (~60 pmol/g with an i.v. administered dose of 600 pmol). Based on a maximum tumor uptake of pretargeted *Proteus*-DOTA of 62 pmol per gram of SW1222 tumor, ~180 nCi of $^{225}$Ac could be localized per gram of tumor at SA that are currently achieved with quantitative RCY.

Accordingly, the compositions of the present technology are useful for in vivo diagnostic imaging methods and pretargeted radioimmunotherapy.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A compound of Formula I

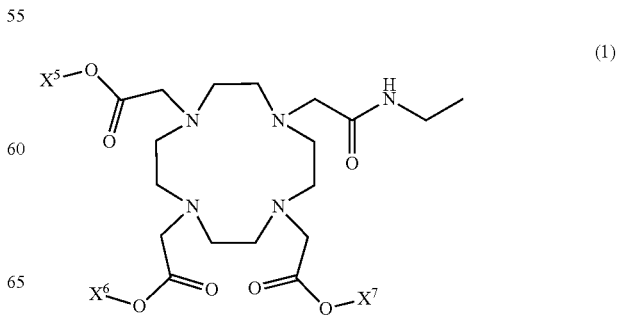

(1)

-continued

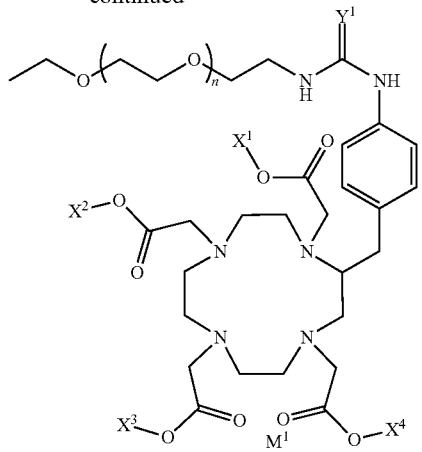

or a pharmaceutically acceptable salt thereof, wherein
M$^1$ is $^{175}$Lu$^{3+}$, $^{45}$Sc$^{3+}$, $^{69}$Ga$^{3+}$, $^{71}$Ga$^{3+}$, $^{89}$Y$^{3+}$, $^{113}$In$^{3+}$, $^{115}$In$^{3+}$, $^{139}$La$^{3+}$, $^{136}$Ce$^{3+}$, $^{138}$Ce$^{3+}$, $^{140}$Ce$^{3+}$, $^{142}$Ce$^{3+}$, $^{151}$Eu$^{3+}$, $^{153}$Eu$^{3+}$, $^{159}$Tb$^{3+}$, $^{154}$Gd$^{3+}$, $^{155}$Gd$^{3+}$, $^{156}$Gd$^{3+}$, $^{157}$Gd$^{3+}$, $^{158}$Gd$^{3+}$, or 160Gd$^{3+}$;

X$^1$, X$^2$, X$^3$, and X$^4$ are each independently a lone pair of electrons or H;

X$^5$, X$^6$, and X$^7$ are each independently a lone pair of electrons or H;

Y$^1$ is O or S; and n is 1, 2, 3, 4, 5, 6, 7, 8, 9, 10, 11, 12, 13, 14, 15, 16, 17, 18, 19, 20, 21, or 22, optionally wherein at least two of X$^1$, X$^2$, X$^3$, and X$^4$ are each independently a lone pair of electrons, or optionally wherein three of X$^1$, X$^2$, X$^3$, and X$^4$ are each independently a lone pair of electrons and the remaining X$^1$, X$^2$, X$^3$, or X$^4$ is H.

2. A bischelate comprising the compound of claim 1 and a radionuclide cation.

3. The bischelate of claim 2, wherein the bischelate is of Formula II

M$^2$ is the radionuclide cation;

X$^1$, X$^2$, X$^3$, and X$^4$ are each independently a lone pair of electrons or H;

X$^5$, X$^6$, and X$^7$ are each independently a lone pair of electrons or H;

Y$^1$ is O or S; and n is 1, 2, 3, 4, 5, 6, 7, 8, 9, 10, 11, 12, 13, 14, 15, 16, 17, 18, 19, 20, 21, or 22, optionally wherein at least two of X$^5$, X$^6$, and X$^7$ are each independently a lone pair of electrons.

4. The bischelate of claim 2, wherein the radionuclide cation is a divalent cation, a trivalent cation, an alpha particle-emitting isotope, a beta particle-emitting isotope, an Auger-emitter, $^{68}$Ga, $^{227}$Th, or $^{64}$Cu.

5. A complex comprising the compound of claim 1 and an anti-tumor antigen bispecific antibody.

6. A complex comprising the bischelate of claim 2 and an anti-tumor antigen bispecific antibody.

7. A method for detecting solid tumors in a subject in need thereof comprising
(a) administering an effective amount of the complex of claim 6 to the subject; and
(b) detecting the presence of solid tumors expressing the tumor antigen in the subject by detecting radioactive levels emitted by the complex that are higher than a reference value, optionally wherein the radioactive levels emitted by the complex are detected using positron emission tomography or single photon emission computed tomography.

8. A method for selecting a subject for pretargeted radioimmunotherapy comprising
(a) administering an effective amount of the complex of claim 6 to the subject;
(b) detecting the presence of solid tumors expressing the tumor antigen in the subject by detecting radioactive levels emitted by the complex; and
(c) selecting the subject for pretargeted radioimmunotherapy when the radioactive levels emitted by the complex are higher than a reference value, optionally wherein the radioactive levels emitted by the complex

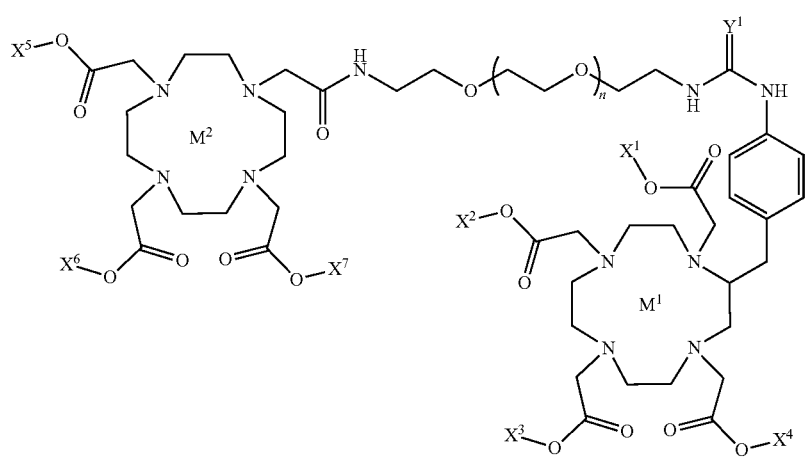

(II)

or a pharmaceutically acceptable salt thereof, wherein
M$^1$ is $^{175}$Lu$^{3+}$, $^{45}$Sc$^{3+}$, $^{69}$Ga$^{3+}$, $^{71}$Ga$^{3+}$, $^{89}$Y$^{3+}$, $^{113}$In$^{3+}$, $^{115}$In$^{3+}$, $^{139}$La$^{3+}$, $^{136}$Ce$^{3+}$, $^{138}$Ce$^{3+}$, $^{140}$Ce$^{3+}$, $^{142}$Ce$^{3+}$, $^{151}$Eu$^{3+}$, $^{153}$Eu$^{3+}$, $^{159}$Tb$^{3+}$, $^{154}$Gd$^{3+}$, $^{155}$Gd$^{3+}$, $^{156}$Gd$^{3+}$, $^{157}$Gd$^{3+}$, $^{158}$Gd$^{3+}$, or 60Gd$^{3+}$;

are detected using positron emission tomography or single photon emission computed tomography.

9. The method of claim 8, wherein the subject is diagnosed with, or is suspected of having a cancer selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, and head-and-neck cancer.

10. The method of claim 7, wherein the complex is administered into the cerebral spinal fluid or blood of the subject or wherein the complex is administered intravenously, intramuscularly, intraarterially, intrathecally, intracapsularly, intraorbitally, intradermally, intraperitoneally, transtracheally, subcutaneously, intracerebroventricularly, orally or intranasally.

11. The method of claim 8, wherein the complex is administered intravenously, intramuscularly, intraarterially, intrathecally, intracapsularly, intraorbitally, intradermally, intraperitoneally, transtracheally, subcutaneously, intracerebroventricularly, orally or intranasally or wherein the complex is administered into the cerebral spinal fluid or blood of the subject.

12. A method for increasing tumor sensitivity to radiation therapy in a subject diagnosed with cancer comprising
(a) administering an effective amount of an anti-DOTA bispecific antibody to the subject, wherein the anti-DOTA bispecific antibody binds to a tumor expressing a tumor antigen target; and
(b) administering an effective amount of the bischelate of claim 2 to the subject, wherein the bischelate binds to the anti-DOTA bispecific antibody.

13. The method of claim 12, further comprising administering an effective amount of a clearing agent to the subject prior to administration of the bischelate, wherein the clearing agent is a 500 kD aminodextran-DOTA conjugate.

14. The method of claim 12, wherein the tumor antigen target is selected from the group consisting of GPA33, HER2/neu, GD2, MAGE-1, MAGE-3, BAGE, GAGE-1, GAGE-2, MUM-1, CDK4, N-acetylglucoaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM.

15. The method of claim 12, wherein the anti-DOTA bispecific antibody and/or the bischelate is administered intravenously, intramuscularly, intraarterially, intrathecally, intracapsularly, intraorbitally, intradermally, intraperitoneally, transtracheally, subcutaneously, intracerebroventricularly, orally or intranasally.

16. A method for increasing tumor sensitivity to radiation therapy in a subject diagnosed with cancer comprising
administering an effective amount of the complex of claim 6 to the subject.

17. A method for treating cancer in a subject in need thereof comprising
(a) administering an effective amount of an anti-DOTA bispecific antibody to the subject, wherein the anti-DOTA bispecific antibody binds to a tumor expressing a tumor antigen target; and
(b) administering an effective amount of the bischelate of claim 2 to the subject, wherein the bischelate binds to the anti-DOTA bispecific antibody.

18. A method for treating cancer in a subject in need thereof comprising
administering an effective amount of the complex of claim 6 to the subject.

19. A kit comprising a bischelate of claim 2, at least one anti-DOTA BsAb, and instructions for use.

20. The kit of claim 19 further comprising a clearing agent and/or one or more radionuclides, wherein the clearing agent is a 500 kD aminodextran-DOTA conjugate.

21. The bischelate of claim 4, wherein
the alpha particle-emitting isotope is selected from the group consisting of $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm; or
the beta particle-emitting isotope is selected from the group consisting of $^{86}$Y, $^{90}$Y, $^{89}$Sr, $^{165}$Dy, $^{186}$Re, $^{188}$Re, $^{177}$Lu, and $^{67}$Cu; or
the Auger-emitter is selected from the group consisting of $^{111}$In, $^{67}$Ga, $^{51}$Cr, $^{58}$Co, $^{99}$mTc, $^{103}$mRh, $^{195}$mPt, $^{119}$Sb, $^{161}$Ho, $^{189}$mOs, $^{192}$Ir, $^{201}$Tl, and $^{203}$Pb.

22. The complex of claim 5, wherein the tumor antigen is selected from the group consisting of GPA33, HER2/neu, GD2, MAGE-1, MAGE-3, BAGE, GAGE-1, GAGE-2, MUM-1, CDK4, N-acetylglucoaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAIVIE (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM.

23. The complex of claim 6, wherein the tumor antigen is selected from the group consisting of GPA33, HER2/neu, GD2, MAGE-1, MAGE-3, BAGE, GAGE-1, GAGE-2, MUM-1, CDK4, N-acetylglucoaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAIVIE (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM.

* * * * *